(12) United States Patent
Abdul-Hafiz et al.

(10) Patent No.: US 11,877,867 B2
(45) Date of Patent: Jan. 23, 2024

(54) PHYSIOLOGICAL MEASUREMENT DEVICE

(71) Applicant: MASIMO CORPORATION, Irvine, CA (US)

(72) Inventors: Yassir Abdul-Hafiz, Irvine, CA (US); Ammar Al-Ali, San Juan Capistrano, CA (US); Kevin Forrest, Rancho Santa Margarita, CA (US); Eugene Mason, La Habra Heights, CA (US); John Schmidt, Lake Forest, CA (US); Virginia Thanh Ta, Santa Ana, CA (US)

(73) Assignee: Masimo Corporation, Irvine, CA (US)

( * ) Notice: Subject to any disclaimer, the term of this patent is extended or adjusted under 35 U.S.C. 154(b) by 163 days.

(21) Appl. No.: 17/381,086

(22) Filed: Jul. 20, 2021

(65) Prior Publication Data
US 2021/0345966 A1 Nov. 11, 2021

Related U.S. Application Data

(63) Continuation of application No. 17/360,570, filed on Jun. 28, 2021, now Pat. No. 11,432,771, which is a
(Continued)

(51) Int. Cl.
*A61B 5/1455* (2006.01)
*A61B 5/00* (2006.01)
(Continued)

(52) U.S. Cl.
CPC .......... *A61B 5/6867* (2013.01); *A61B 5/0205* (2013.01); *A61B 5/0261* (2013.01);
(Continued)

(58) Field of Classification Search
CPC .............. A61B 5/1455; A61B 5/14551; A61B 5/14552; A61B 5/6817
See application file for complete search history.

(56) References Cited

U.S. PATENT DOCUMENTS 3,029,682 A 4/1962 Wood
3,815,583 A 6/1974 Scheidt
(Continued)

FOREIGN PATENT DOCUMENTS

CN 2142625 9/1993
CN 200954107 10/2007
(Continued)

OTHER PUBLICATIONS

US 9,579,050 B2, 02/2017, Al-Ali (withdrawn)
(Continued)

*Primary Examiner* — Marjan Fardanesh
(74) *Attorney, Agent, or Firm* — Knobbe, Martens, Olson & Bear, LLP

(57) ABSTRACT

An physiological measurement device provides a device body having a base, legs extending from the base and an optical housing disposed at ends of the legs opposite the base. An optical assembly is disposed in the housing. The device body is flexed so as to position the housing over a tissue site. The device body is unflexed so as to attach the housing to the tissue site and position the optical assembly to illuminate the tissue site. The optical assembly is configured to transmit optical radiation into tissue site tissue and receive the optical radiation after attenuation by pulsatile blood flow within the tissue.

20 Claims, 31 Drawing Sheets

Related U.S. Application Data continuation of application No. 16/377,772, filed on Apr. 8, 2019, now Pat. No. 11,426,125, which is a continuation of application No. 15/417,640, filed on Jan. 27, 2017, now Pat. No. 10,292,657, which is a continuation of application No. 14/218,328, filed on Mar. 18, 2014, now abandoned, which is a continuation of application No. 13/975,008, filed on Aug. 23, 2013, now Pat. No. 9,259,185, which is a continuation of application No. 12/658,872, filed on Feb. 16, 2010, now Pat. No. 8,588,880.

(60) Provisional application No. 61/152,964, filed on Feb. 16, 2009.

(51) Int. Cl.
  *A61B 5/0205* (2006.01)
  *A61B 5/024* (2006.01)
  *A61B 5/026* (2006.01)

(52) U.S. Cl.
  CPC ........ *A61B 5/02427* (2013.01); *A61B 5/1455* (2013.01); *A61B 5/14552* (2013.01); *A61B 5/6815* (2013.01); *A61B 5/6816* (2013.01); *A61B 5/6817* (2013.01); *A61B 5/6838* (2013.01)

(56) References Cited

U.S. PATENT DOCUMENTS

| | | |
|---|---|---|
| 3,909,556 A | 9/1975 | Johanson |
| 3,975,599 A | 8/1976 | Johanson |
| 4,550,227 A | 10/1985 | Topholm |
| 4,629,833 A | 12/1986 | Kern et al. |
| 4,638,125 A | 1/1987 | Buettner |
| 4,680,799 A | 7/1987 | Henneberger |
| 4,689,819 A | 8/1987 | Killion |
| 4,723,293 A | 2/1988 | Harless |
| 4,739,512 A | 4/1988 | Hartl et al. |
| 4,764,957 A | 8/1988 | Angelini et al. |
| 4,955,729 A | 9/1990 | Marx |
| 4,960,128 A | 10/1990 | Gordon et al. |
| 4,964,408 A | 10/1990 | Hink et al. |
| 4,985,925 A | 1/1991 | Langberg et al. |
| 5,003,608 A | 3/1991 | Carlson |
| 5,041,187 A | 8/1991 | Hink et al. |
| 5,069,213 A | 12/1991 | Hink et al. |
| 5,163,438 A | 11/1992 | Gordon et al. |
| 5,210,803 A | 5/1993 | Martin et al. |
| 5,213,099 A | 5/1993 | Tripp, Jr. |
| 5,228,089 A | 7/1993 | Inanaga et al. |
| 5,239,588 A | 8/1993 | Davis |
| 5,319,355 A | 6/1994 | Russek |
| 5,333,622 A | 8/1994 | Casali et al. |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,372,134 A | 12/1994 | Richardson |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,524,150 A | 6/1996 | Sauer |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,642,426 A | 6/1997 | Neuman et al. |
| 5,645,440 A | 7/1997 | Tobler et al. |
| 5,659,621 A | 8/1997 | Newton |
| 5,671,914 A | 9/1997 | Kalkhoran et al. |
| 5,673,692 A | 10/1997 | Schulze et al. |
| 5,685,299 A | 11/1997 | Diab et al. |
| 5,721,783 A | 2/1998 | Anderson |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,078,829 A | 6/2000 | Uchida |
| 6,080,110 A | 6/2000 | Thorgersen |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |

(56) References Cited

U.S. PATENT DOCUMENTS

| | | |
|---|---|---|
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,556,852 B1 | 4/2003 | Schulze et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,745,764 B2 | 6/2004 | Hickle |
| 6,760,607 B2 | 7/2004 | Al-Ali |
| D495,317 S | 8/2004 | Sugioka et al. |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,808,473 B2 | 10/2004 | Hisano et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,175,601 B2 | 2/2007 | Verjus et al. |
| 7,186,966 B2 | 3/2007 | Al-Ali |
| 7,190,261 B2 | 3/2007 | Al-Ali |
| 7,209,775 B2 | 4/2007 | Bae et al. |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,263,396 B2 | 8/2007 | Chen et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |

(56) References Cited

U.S. PATENT DOCUMENTS

| | | |
|---|---|---|
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,386,347 B2 | 6/2008 | Chung et al. |
| 7,395,158 B2 | 7/2008 | Monfre et al. |
| 7,412,272 B2 | 8/2008 | Medina |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,522,739 B2 | 4/2009 | Rass et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,769,435 B2 | 8/2010 | Kuo et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,914,468 B2 | 3/2011 | Shalon et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,986,803 B1 | 7/2011 | DeKalb |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,108,036 B2 | 1/2012 | Tran |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,199,956 B2 | 6/2012 | Haartsen et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,251,903 B2 | 8/2012 | LeBoeuf et al. |
| 8,255,026 B1 | 8/2012 | Ai-Ai |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,271,075 B2 | 9/2012 | Chuang et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| 8,320,982 B2 | 11/2012 | LeBoeuf et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,375 B2 | 2/2013 | Hu |

(56) References Cited

U.S. PATENT DOCUMENTS

| | | |
|---|---|---|
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,406,447 B2 | 3/2013 | Kromann et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,439 B2 | 7/2013 | Bae et al. |
| 8,498,684 B2 | 7/2013 | Weber et al. |
| 8,504,128 B2 | 8/2013 | Blank et al. |
| 8,506,469 B2 | 8/2013 | Dietrich et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,574,165 B2 | 11/2013 | Marsh |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,436 B2 | 1/2014 | Berg |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,647,270 B2 | 2/2014 | LeBoeuf et al. |
| 8,652,040 B2 | 2/2014 | LeBoeuf et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,718,980 B2 | 5/2014 | Garudadri et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,737,669 B2 | 5/2014 | Monahan et al. |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,774,435 B2 | 7/2014 | Ambrose et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,897,859 B2 | 11/2014 | Shimuta et al. |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,923,918 B2 | 12/2014 | Kreger et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,082,388 B2 | 7/2015 | Annunziato et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |

(56) References Cited

U.S. PATENT DOCUMENTS

| | | |
|---|---|---|
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| D740,255 S | 10/2015 | Samrelius |
| 9,153,112 B1 | 10/2015 | Kiani et al. |
| 9,153,121 B2 | 10/2015 | Kiani et al. |
| 9,161,114 B2 | 10/2015 | Bone et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,313,585 B2 | 4/2016 | Lunner |
| 9,323,894 B2 | 4/2016 | Kiani |
| 9,323,899 B2 | 4/2016 | Goldstein |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,398,891 B2 | 7/2016 | Bagha |
| 9,408,542 B1 | 8/2016 | Kinast et al. |
| 9,436,645 B2 | 9/2016 | Al-Ali et al. |
| 9,438,294 B2 | 9/2016 | Boesen |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,602,938 B2 | 3/2017 | Goldstein et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al Ali et al. |
| 9,636,056 B2 | 5/2017 | Al-Ali |
| 9,649,054 B2 | 5/2017 | Lamego et al. |
| 9,658,825 B2 | 5/2017 | Garudadri et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,699,546 B2 | 7/2017 | Qian et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,736,569 B2 | 8/2017 | Kelly et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,774,963 B1 | 9/2017 | Han |
| 9,775,520 B2 | 10/2017 | Tran |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,808,199 B2 | 11/2017 | Kilsgaard et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |
| 9,848,807 B2 | 12/2017 | Lamego |
| D808,934 S | 1/2018 | Tang et al. |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,900,687 B2 | 2/2018 | Sorensen |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,312 B2 | 4/2018 | Meskens et al. |
| 9,936,917 B2 | 4/2018 | Poeze et al. |
| 9,937,355 B2 | 4/2018 | Kaib et al. |
| 9,943,269 B2 | 4/2018 | Muhsin et al. |
| 9,949,676 B2 | 4/2018 | Al-Ali |
| D817,309 S | 5/2018 | Czaniecki et al. |

(56) References Cited

U.S. PATENT DOCUMENTS

| | | |
|---|---|---|
| 9,955,919 B2 | 5/2018 | LeBoeuf et al. |
| 9,955,937 B2 | 5/2018 | Telfort |
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| D826,211 S | 8/2018 | Kim |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,037 B1 | 12/2018 | Chen |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,657 B2 | 5/2019 | Abdul-Hafiz et al. |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,362,384 B2 | 7/2019 | Yun |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,433,045 B2 | 10/2019 | Trainer et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| D868,752 S | 12/2019 | Zhu |
| D870,708 S | 12/2019 | Lindenberger |
| D871,376 S | 12/2019 | Zhou |
| 10,499,183 B2 | 12/2019 | Zellner |
| 10,505,311 B2 | 12/2019 | Al-Ali et al. |
| 10,511,901 B2 | 12/2019 | Garrett |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| D879,074 S | 3/2020 | Komiya et al. |
| 10,602,255 B2 | 3/2020 | Sandanger |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D883,257 S | 5/2020 | Duddy |
| D885,372 S | 5/2020 | Wang |
| 10,639,468 B2 | 5/2020 | Cook et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| 10,681,445 B2 | 6/2020 | Hatfield et al. |
| D889,441 S | 7/2020 | Lin |
| D890,708 S | 7/2020 | Forrest et al. |
| D890,727 S | 7/2020 | Park et al. |
| 10,721,785 B2 | 7/2020 | Al-Ali |
| 10,728,645 B2 | 7/2020 | Briggs et al. |
| D894,158 S | 8/2020 | Gu |
| 10,736,518 B2 | 8/2020 | Al-Ali et al. |
| 10,750,984 B2 | 8/2020 | Pauley et al. |
| D895,578 S | 9/2020 | Yang |
| D896,205 S | 9/2020 | Zhang et al. |
| D897,098 S | 9/2020 | Al-Ali |
| D897,319 S | 9/2020 | Wang |
| 10,779,098 B2 | 9/2020 | Iswanto et al. |
| 10,791,390 B2 | 9/2020 | Karayiannis et al. |
| D902,184 S | 11/2020 | Yang |
| 10,827,249 B1 | 11/2020 | Pine et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,834,492 B2 | 11/2020 | Feng et al. |
| D904,349 S | 12/2020 | Saxton et al. |
| D906,298 S | 12/2020 | Wang |
| 10,849,554 B2 | 12/2020 | Shreim et al. |
| 10,856,750 B2 | 12/2020 | Indorf |
| 10,869,115 B2 | 12/2020 | Cohen et al. |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| 10,959,639 B2 | 3/2021 | Kidmose et al. |
| D916,135 S | 4/2021 | Indorf et al. |
| D917,046 S | 4/2021 | Abdul-Hafiz et al. |
| D917,425 S | 4/2021 | Wang |
| D917,550 S | 4/2021 | Indorf et al. |
| D917,564 S | 4/2021 | Indorf et al. |
| D917,704 S | 4/2021 | Al-Ali et al. |
| 10,984,776 B2 | 4/2021 | Yamkovoy |
| 10,987,005 B2 | 4/2021 | LeBoeuf et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| D920,288 S | 5/2021 | Vautour |
| 11,006,867 B2 | 5/2021 | Al-Ali |
| D921,202 S | 6/2021 | Al-Ali et al. |
| D922,985 S | 6/2021 | Kataoa |
| D923,610 S | 6/2021 | Bonahoom et al. |
| 11,024,064 B2 | 6/2021 | Muhsin et al. |

(56) References Cited

U.S. PATENT DOCUMENTS

| | | |
|---|---|---|
| 11,026,023 B2 | 6/2021 | Wang et al. |
| 11,026,604 B2 | 6/2021 | Chen et al. |
| D924,848 S | 7/2021 | Yang |
| D925,597 S | 7/2021 | Chandran et al. |
| D927,699 S | 8/2021 | Al-Ali et al. |
| D928,122 S | 8/2021 | Yoshida et al. |
| D928,742 S | 8/2021 | Liu |
| 11,076,777 B2 | 8/2021 | Lee et al. |
| 11,095,973 B1 | 8/2021 | Zalisk et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| D939,479 S | 12/2021 | Wang et al. |
| 11,191,484 B2 | 12/2021 | Kiani et al. |
| D941,278 S | 1/2022 | Laffon de Mazieres et al. |
| 11,252,494 B2 | 2/2022 | Mori |
| D945,404 S | 3/2022 | Birger |
| D945,405 S | 3/2022 | Rose et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,266,531 B2 | 3/2022 | Aceti et al. |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| 11,317,185 B2 | 4/2022 | Imamura |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,389,093 B2 | 7/2022 | Triman et al. |
| D959,411 S | 8/2022 | Ando et al. |
| 11,406,286 B2 | 8/2022 | Al-Ali et al. |
| 11,417,426 B2 | 8/2022 | Muhsin et al. |
| 11,425,484 B2 | 8/2022 | Kim et al. |
| 11,426,125 B2 | 8/2022 | Abdul-Hafiz et al. |
| 11,432,771 B2 | 9/2022 | Abdul-Hafiz et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2003/0220584 A1 | 11/2003 | Honeyager et al. |
| 2004/0106163 A1 | 6/2004 | Workman, Jr. et al. |
| 2005/0033131 A1 | 2/2005 | Chen et al. |
| 2005/0055276 A1 | 3/2005 | Kiani et al. |
| 2005/0124375 A1 | 6/2005 | Nowosielski |
| 2005/0209516 A1 | 9/2005 | Fraden |
| 2005/0234317 A1 | 10/2005 | Kiani |
| 2006/0045304 A1 | 3/2006 | Lee et al. |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2007/0032715 A1 | 2/2007 | Eghbal et al. |
| 2007/0032731 A1 | 2/2007 | Lovejoy et al. |
| 2007/0073116 A1 | 3/2007 | Kiani et al. |
| 2007/0078315 A1 | 4/2007 | Kling et al. |
| 2007/0180140 A1 | 8/2007 | Welch et al. |
| 2007/0197881 A1 | 8/2007 | Wolf et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0076972 A1 | 3/2008 | Dorogusker et al. |
| 2008/0094228 A1 | 4/2008 | Welch et al. |
| 2008/0154098 A1 | 6/2008 | Morris et al. |
| 2008/0177162 A1 | 7/2008 | Bae et al. |
| 2008/0205679 A1 | 8/2008 | Darbut et al. |
| 2008/0221418 A1 | 9/2008 | Al-Ali et al. |
| 2009/0010461 A1 | 1/2009 | Klinghult |
| 2009/0024004 A1 | 1/2009 | Yang |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0160714 A1 | 6/2010 | Chua et al. |
| 2010/0197360 A1 | 8/2010 | Namgoong et al. |
| 2010/0234718 A1 | 9/2010 | Sampath et al. |
| 2010/0270257 A1 | 10/2010 | Wachman et al. |
| 2010/0274109 A1 | 10/2010 | Hu et al. |
| 2010/0308999 A1 | 12/2010 | Chornenky |
| 2010/0331631 A1 | 12/2010 | MacLaughlin |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0125060 A1 | 5/2011 | Telfort et al. |
| 2011/0137141 A1 | 6/2011 | Razoumov et al. |
| 2011/0137297 A1 | 6/2011 | Kiani et al. |
| 2011/0144779 A1 | 6/2011 | Janse et al. |
| 2011/0166624 A1 | 7/2011 | Dietrich et al. |
| 2011/0172498 A1 | 7/2011 | Olsen et al. |
| 2011/0208015 A1 | 8/2011 | Welch et al. |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |

(56) References Cited

U.S. PATENT DOCUMENTS

| | | |
|---|---|---|
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187885 A1 | 7/2014 | Kreuzer |
| 2014/0187973 A1 | 7/2014 | Brown et al. |
| 2014/0213864 A1 | 7/2014 | Abdul-Hafiz et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank et al. |
| 2016/0029932 A1 | 2/2016 | Al-Ali |
| 2016/0058347 A1 | 3/2016 | Reichgott et al. |
| 2016/0066080 A1 | 3/2016 | Kolton |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0166182 A1 | 6/2016 | Al-Ali et al. |
| 2016/0166183 A1 | 6/2016 | Poeze et al. |
| 2016/0173969 A1 | 6/2016 | DeKalb |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali |
| 2017/0340293 A1 | 11/2017 | Al-Ali et al. |
| 2017/0360310 A1 | 12/2017 | Kiani |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |

(56) References Cited

U.S. PATENT DOCUMENTS

| | | |
|---|---|---|
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2018/0317841 A1 | 11/2018 | Novak, Jr. |
| 2018/0332379 A1 | 11/2018 | McGarry et al. |
| 2018/0333055 A1 | 11/2018 | Lamego et al. |
| 2018/0333087 A1 | 11/2018 | Al-Ali |
| 2018/0352338 A1 | 12/2018 | Murarka et al. |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0029593 A1 | 1/2019 | Orron et al. |
| 2019/0038143 A1 | 2/2019 | Al-Ali |
| 2019/0058280 A1 | 2/2019 | Al-Ali et al. |
| 2019/0058281 A1 | 2/2019 | Al-Ali et al. |
| 2019/0117070 A1 | 4/2019 | Muhsin et al. |
| 2019/0231270 A1 | 8/2019 | Abdul-Hafiz et al. |
| 2019/0239787 A1 | 8/2019 | Pauley et al. |
| 2019/0239796 A1 | 8/2019 | Avrahamson |
| 2019/0320906 A1 | 10/2019 | Olsen |
| 2019/0374139 A1 | 12/2019 | Kiani et al. |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0321946 A1 | 10/2021 | Abdul-Hafiz et al. |
| 2021/0330228 A1 | 10/2021 | Olsen et al. |
| 2021/0386382 A1 | 12/2021 | Olsen et al. |
| 2021/0390941 A1 | 12/2021 | Lakshminarayanan et al. |
| 2021/0402110 A1 | 12/2021 | Pauley et al. |
| 2022/0007097 A1 | 1/2022 | Ko et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0060807 A1 | 2/2022 | Wei |
| 2022/0071562 A1 | 3/2022 | Kiani |
| 2022/0095040 A1 | 3/2022 | Holley et al. |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0248120 A1 | 8/2022 | Ito et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0145155 A1 | 5/2023 | Krishnamani et al. |

FOREIGN PATENT DOCUMENTS

| | | |
|---|---|---|
| CN | 201105090 | 8/2008 |
| CN | 201230878 | 5/2009 |
| CN | 201280178 | 7/2009 |
| CN | 101530647 | 9/2009 |
| CN | 101708121 | 5/2010 |
| DE | 35 05 099 | 9/1985 |
| DE | 37 23 809 | 1/1989 |
| DE | 20 2004 018 615 | 4/2006 |
| EM | D006885901-0001 | 9/2019 |
| EM | D006636254-0001 | 10/2019 |
| EM | D006772273-0002 | 10/2019 |
| EM | D007538657-0002 | 2/2020 |
| EM | D006523809-0001 | 3/2020 |
| EM | D007725007-0001 | 3/2020 |
| EM | D007735212-0001 | 3/2020 |
| EM | D007719497-0002 | 4/2020 |
| EM | D007223698-0001 | 5/2020 |
| EM | D007984109-0001 | 6/2020 |
| EM | D007797287-0009 | 7/2020 |
| EM | D007797287-0010 | 7/2020 |
| EM | D008053755-0002 | 7/2020 |
| EM | D008053755-0003 | 7/2020 |
| EM | D008086896-0001 | 8/2020 |
| EM | D008086896-0002 | 8/2020 |
| EM | D008099535-0001 | 9/2020 |
| EM | D008166235-0002 | 9/2020 |
| EM | D007290614-0006 | 10/2020 |
| EM | D008129456-0001 | 10/2020 |
| EM | D008172480-0002 | 10/2020 |
| EM | D008025118-0007 | 11/2020 |
| EM | D008025118-0008 | 11/2020 |
| EM | D008025118-0009 | 11/2020 |
| EM | D008025118-0010 | 11/2020 |
| EM | D008277826-0001 | 12/2020 |
| EM | D008150452-0002 | 1/2021 |
| EM | D008368757-0001 | 1/2021 |
| EM | D008499883-0001 | 4/2021 |
| EM | D008534457-0001 | 5/2021 |
| EM | D008559868-0001 | 6/2021 |
| EM | D008599195-0002 | 7/2021 |
| EM | D008324495-0002 | 9/2021 |

(56) References Cited

FOREIGN PATENT DOCUMENTS

| | | |
|---|---|---|
| EM | D008656482-0011 | 2/2022 |
| EM | D008860423-0005 | 4/2022 |
| EM | D008860423-0006 | 4/2022 |
| EM | D009074032-0001 | 7/2022 |
| EM | D009074032-0002 | 7/2022 |
| EM | D009079510-0001 | 7/2022 |
| EM | D009101983-0002 | 8/2022 |
| EP | 2 116 183 | 11/2009 |
| EP | 2 214 554 | 1/2012 |
| GB | 09166 | 7/1914 |
| JP | 61-279222 | 12/1986 |
| JP | 63-102767 | 5/1988 |
| JP | 63-292799 | 11/1988 |
| JP | 04-242400 | 8/1992 |
| JP | 3013262 | 7/1995 |
| JP | 08-195999 | 7/1996 |
| JP | 09-253062 | 9/1997 |
| JP | 10-239158 | 9/1998 |
| JP | 2837641 | 12/1998 |
| JP | 2905116 | 6/1999 |
| JP | 2002-000576 | 1/2002 |
| JP | 2007-021106 | 2/2007 |
| JP | 2007-215722 | 8/2007 |
| JP | 2008-136556 | 6/2008 |
| JP | 2008-219586 | 9/2008 |
| JP | 2009-082263 | 4/2009 |
| JP | 4952244 | 6/2012 |
| KR | 10-2005-0099444 | 10/2005 |
| KR | 10-2006-0002448 | 1/2006 |
| KR | 10-2006-0007334 | 1/2006 |
| KR | 10-0561091 | 3/2006 |
| KR | 10-0677583 | 2/2007 |
| KR | 10-2008-0088217 | 10/2008 |
| KR | 10-0958106 | 5/2010 |
| KR | 10-1020508 | 3/2011 |
| KR | 10-1030887 | 4/2011 |
| KR | 10-2011-0052783 | 5/2011 |
| KR | 10-1044883 | 6/2011 |
| KR | 10-1225554 | 1/2013 |
| TW | M344138 | 11/2008 |
| TW | M348587 | 1/2009 |
| TW | M360013 | 7/2009 |
| WO | WO 95/015067 | 6/1995 |
| WO | WO 99/062403 | 12/1999 |
| WO | WO 2007/050487 | 5/2007 |
| WO | WO 2007/100959 | 9/2007 |
| WO | WO 2009/001449 | 12/2008 |
| WO | WO 2009/033181 | 3/2009 |
| WO | WO 2010/079257 | 7/2010 |
| WO | WO 2010/108287 | 9/2010 |
| WO | WO 2011/102846 | 8/2011 |
| WO | WO 2021/263098 | 12/2021 |

OTHER PUBLICATIONS

International Search Report and Written Opinion as received in PCT Application No. PCT/US2010/033796 dated Oct. 17, 2011, pp. 13.
Ear Sensor, U.S. Appl. No. 12/658,872, U.S. Pat. No. 8,588,880.
Ear Sensor, U.S. Appl. No. 13/975,008, U.S. Pat. No. 9,259,185.
Ear Sensor, U.S. Appl. No. 14/218,328, 2014/0213864.
Ear Sensor, U.S. Appl. No. 15/417,640, U.S. Pat. No. 10,292,657.
Physiological Measurement Device, U.S. Appl. No. 16/377,772, 2019/0231270.
Physiological Measurement Device, U.S. Appl. No. 17/360,570, 2021/0321946.

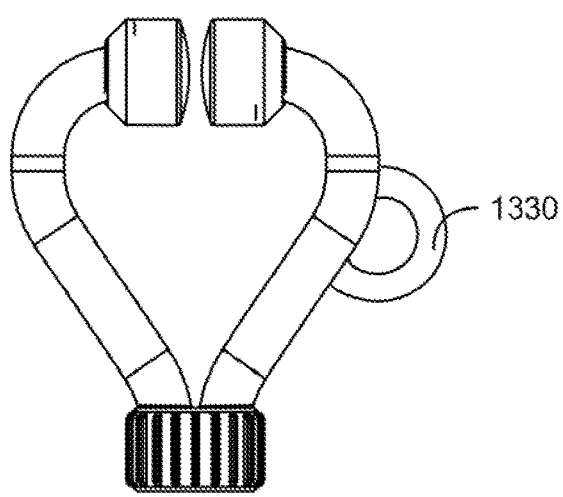
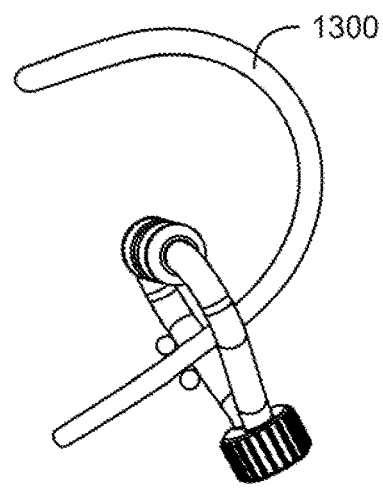
FIG. 13D  FIG. 13E
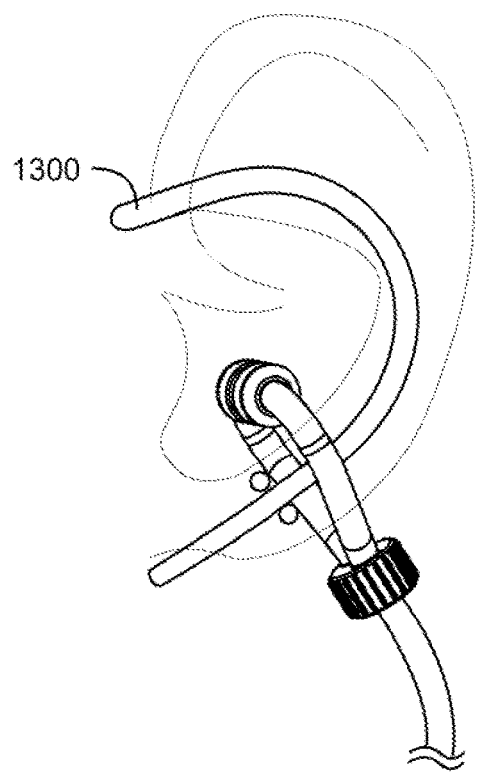
FIG. 13F

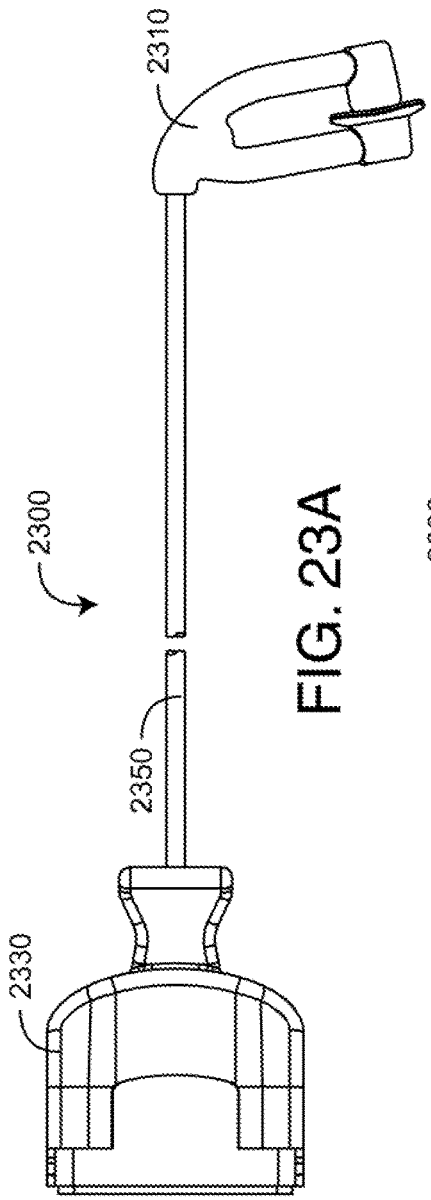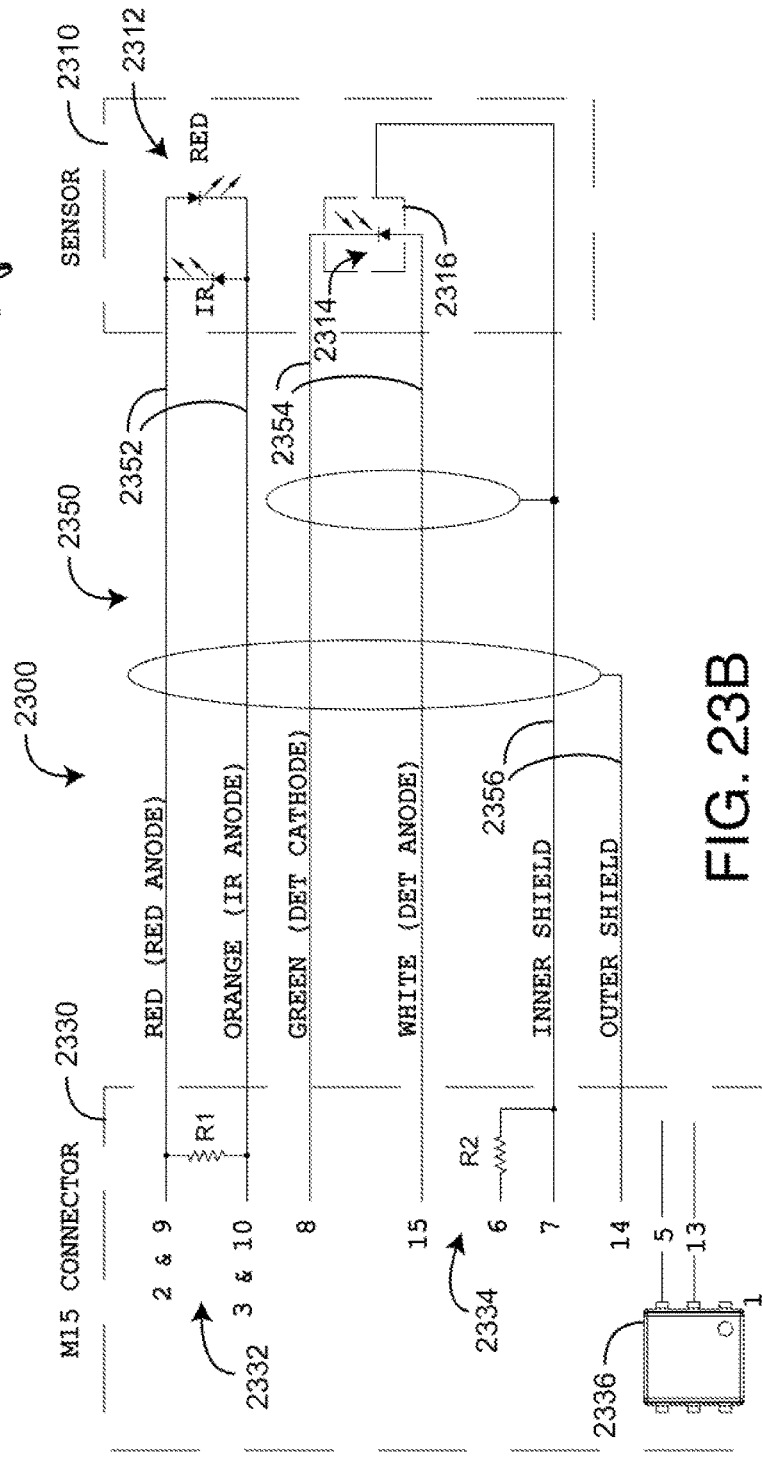

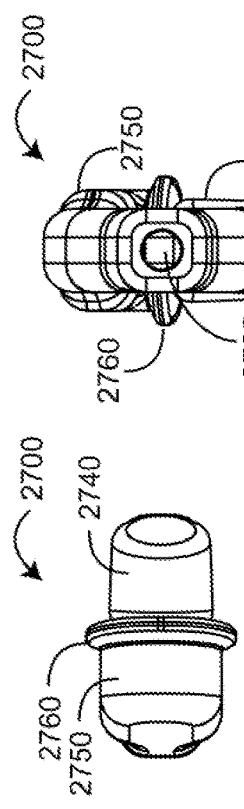
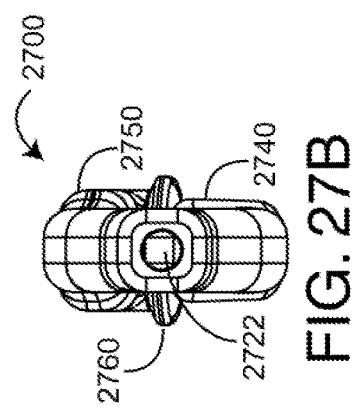
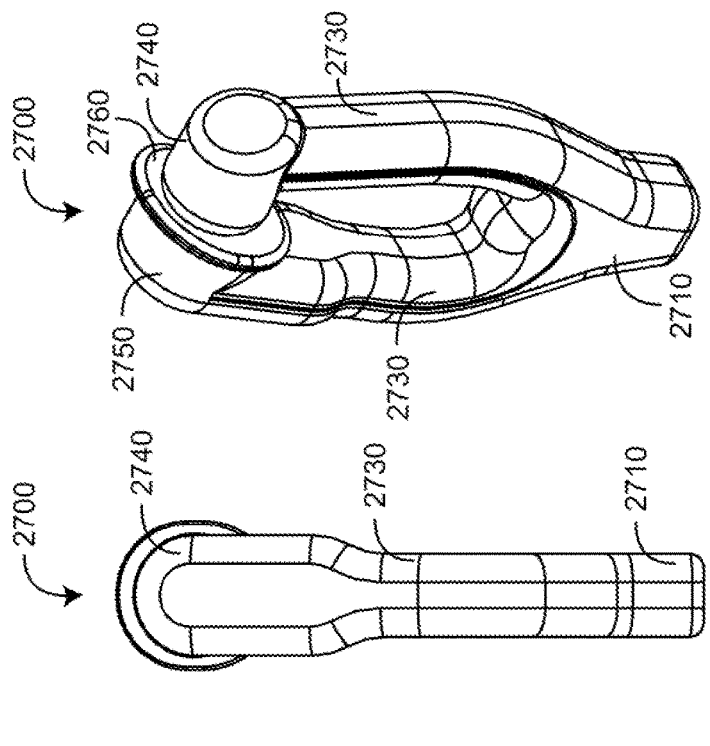
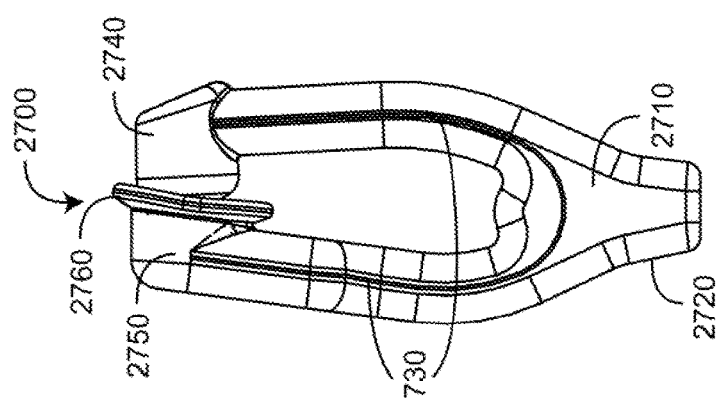
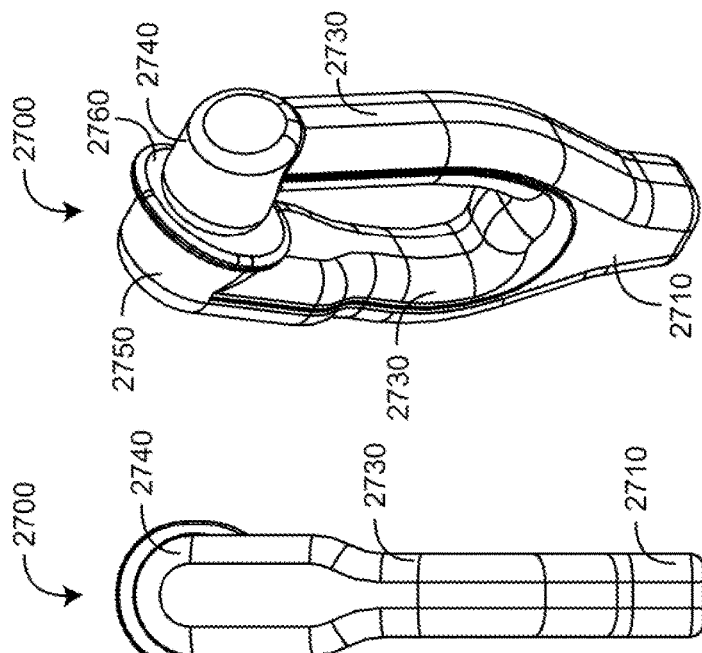
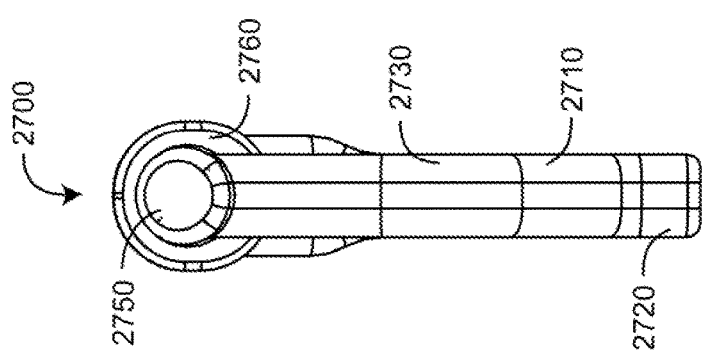

PHYSIOLOGICAL MEASUREMENT DEVICE

CROSS-REFERENCE TO RELATED APPLICATIONS

The present application is a continuation of U.S. patent application Ser. No. 17/360,570, filed Jun. 28, 2021, titled "PHYSIOLOGICAL MEASUREMENT DEVICE", which is a continuation of U.S. patent application Ser. No. 16/377,772, filed Apr. 8, 2019, titled "PHYSIOLOGICAL MEASUREMENT DEVICE," which is a continuation of U.S. patent application Ser. No. 15/417,640, filed Jan. 27, 2017, titled "Ear Sensor," which is a continuation of U.S. patent application Ser. No. 14/218,328, filed Mar. 18, 2014, titled "Ear Sensor," which is a continuation of U.S. patent application Ser. No. 13/975,008, filed Aug. 23, 2013, titled "Ear Sensor," which is a continuation of U.S. patent application Ser. No. 12/658,872, filed Feb. 16, 2010, titled "Ear Sensor," which claims priority benefit under 35 U.S.C. § 119(e) to U.S. Provisional Patent Application No. 61/152,964, filed Feb. 16, 2009, titled "Ear Sensor," each of which is hereby incorporated by reference herein in its entirety.

BACKGROUND OF THE INVENTION

Pulse oximetry systems for measuring constituents of circulating blood have gained rapid acceptance in a wide variety of medical applications, including surgical wards, intensive care and neonatal units, general wards, home care, physical training, and virtually all types of monitoring scenarios. A pulse oximetry system generally includes an optical sensor applied to a patient, a monitor for processing sensor signals and displaying results and a patient cable electrically interconnecting the sensor and the monitor. A pulse oximetry sensor has light emitting diodes (LEDs), typically one emitting a red wavelength and one emitting an infrared (IR) wavelength, and a photodiode detector. The emitters and detector are typically attached to a finger, and the patient cable transmits drive signals to these emitters from the monitor. The emitters respond to the drive signals to transmit light into the fleshy fingertip tissue. The detector generates a signal responsive to the emitted light after attenuation by pulsatile blood flow within the fingertip. The patient cable transmits the detector signal to the monitor, which processes the signal to provide a numerical readout of physiological parameters such as oxygen saturation ($SpO_2$) and pulse rate.

Pulse oximeters capable of reading through motion induced noise are disclosed in at least U.S. Pat. Nos. 6,770,028, 6,658,276, 6,650,917, 6,157,850, 6,002,952, 5,769,785, and 5,758,644; low noise pulse oximetry sensors are disclosed in at least U.S. Pat. No. 6,088,607 and 5,782,757; all of which are assigned to Masimo Corporation, Irvine, Calif. ("Masimo") and are incorporated by reference herein. An ear sensor is disclosed in U.S. Pat. No. 7,341,559 titled *Pulse Oximetry Ear Sensor*, also assigned to Masimo and also incorporated by reference herein.

Advanced physiological monitoring systems may incorporate pulse oximetry in addition to advanced features for the calculation and display of other blood parameters, such as carboxyhemoglobin (HbCO), methemoglobin (HbMet) and total hemoglobin (Hbt), as a few examples. Advanced physiological monitors and corresponding multiple wavelength optical sensors capable of measuring parameters in addition to $SpO_2$, such as HbCO, HbMet and Hbt are described in at least U.S. patent application Ser. No. 12/056,179, filed Mar. 26, 2008, titled *Multiple Wavelength Optical Sensor* and U.S. patent application Ser. No. 11/366,208, filed Mar. 1, 2006, titled Noninvasive Multi-Parameter Patient Monitor, both incorporated by reference herein. Further, noninvasive blood parameter monitors and corresponding multiple wavelength optical sensors, such as Rainbow™ adhesive and reusable sensors and RAD57™ and Radical-7™ monitors for measuring $SpO_2$, pulse rate, perfusion index (PI), signal quality (SiQ), pulse variability index (PVI), HbCO and HbMet among other parameters are also available from Masimo.

SUMMARY OF THE INVENTION

FIG. 1 illustrates various areas of the ear 100 that are amenable to blood parameter measurements, such as oxygen saturation ($SpO_2$). An ear site has the advantage of more quickly and more accurately reflecting oxygenation changes in the body's core as compared to peripheral site measurements, such as a fingertip. Conventional ear sensors utilize a sensor clip on the ear lobe 110. However, significant variations in lobe size, shape and thickness and the general floppiness of the ear lobe render this site less suitable for central oxygen saturation measurements than the concha 120 and the ear canal 130. Disclosed herein are various embodiments for obtaining noninvasive blood parameter measurements from concha 120 and ear canal 130 tissue sites.

One aspect of an ear sensor optically measures physiological parameters related to blood constituents by transmitting multiple wavelengths of light into a concha site and receiving the light after attenuation by pulsatile blood flow within the concha site. The ear sensor comprises a sensor body, a sensor connector and a sensor cable interconnecting the sensor body and the sensor connector. The sensor body comprises a base, legs and an optical assembly. The legs extend from the base to detector and emitter housings. An optical assembly has an emitter and a detector. The emitter is disposed in the emitter housing and the detector is disposed in the detector housing. The legs have an unflexed position with the emitter housing proximate the detector housing and a flexed position with the emitter housing distal the detector housing. The legs are moved to the flexed position so as to position the detector housing and emitter housing over opposite sides of a concha site. The legs are released to the unflexed position so that the concha site is grasped between the detector housing and emitter housing.

In various embodiments, the ear sensor has a resilient frame and a one piece molded skin disposed over the resilient frame. A cup is disposed proximate the detector housing and has a surface that generally conforms to the curvature of the concha site so as to couple the detector to the concha site and so as to block ambient light. A sensor cable has wires extending from one end of the sensor cable and disposed within channels defined by the resilient frame. The wires electrically and mechanically attach to the optical assembly. A connector is attached to the other end of the sensor cable, and the cable wires electrically and mechanically attach to the connector so as to provide communications between the connector and the optical assembly.

In other embodiments, a stabilizer maintains the position of the detector housing and the emitter housing on the concha site. The stabilizer may have a ring that encircles the legs. The ring has a hold position disposed against the legs and a release position spaced from the legs. A release, when pressed, moves the ring from the hold position to the release position, allowing the ring to slidably move along the legs in a direction away from the base so as to increase the force of the emitter housing and detector housing on the concha site in the hold position and in a direction toward the base so as to decrease the force of the emitter housing and the detector housing on the concha site in the hold position. The stabilizer may have an ear hanger that rests along the back of the ear and couples to at least one of the legs and the sensor cable.

Another aspect of an ear sensor comprises providing a sensor body having a base, legs extending from the base and an optical housing disposed at ends of the legs distal the base. An optical assembly is disposed in the housing. The sensor body is flexed so as to position the housing over a concha site. The sensor body is unflexed so as to attach the housing to the concha site and position the optical assembly to illuminate the concha site.

In various embodiments, an ear surface conforming member is molded to at least a portion of the housing so as to physically couple the housing to the concha site and block ambient light from the optical assembly accordingly. The force of the housing against the concha site is adjusted. The adjusting comprises positioning a force adjustment ring on the sensor body so as to encircle the legs. The positioning comprises squeezing a ring release so as to move ring grips away from the legs, moving the force adjustment ring along the legs and toward the housing so as to increase the force of the housing on the concha site, and moving the force adjustment ring along the legs and away from the housing so as to decrease the force of the housing on the concha site.

In other embodiments, an aspect of the ear sensor comprises supporting at least a portion of the weight of the sensor body and corresponding sensor cable so as to reduce the force needed to attach the housing to the concha site. The supporting comprises attaching at least one of the sensor body and sensor cable to an ear hook placed over the ear.

A further aspect of an ear sensor comprising a clip means having a flexed position and an unflexed position. An optical means transmits multiple wavelength light into a tissue site when activated and receives the light after attenuation by pulsatile blood flow within the tissue site. The optical means is disposed on the clip means so that the optical means can be positioned on a concha site in the flexed position and pinched against the concha site in the unflexed position. A connector means mechanically attaches to and electrically communicates with a monitor. A cable means interconnects the connector means with the optical means. In various embodiments, the clip means comprises a resilient frame means for securing the optical means in a fixed position relative to the tissue site. A housing means encloses the resilient frame means and the optical means. A cup means physically couples at least a portion of the optical means to the concha site and blocks ambient light from the optical means. An adjustable force means holds the clip means to the concha site. Alternatively, or in addition to, a support means holds the clip means to the concha site.

BRIEF DESCRIPTION OF THE DRAWINGS

FIGS. 2A-B are a side view and a perspective view of an ear bud embodiment of an ear sensor;

FIGS. 3A-B are perspective views of a flexible ear pad embodiment of an ear sensor;

FIGS. 4A-D are side views of "C"-clip embodiments for attaching an ear sensor to a concha site;

FIGS. 5A-B are perspective views of alligator clip embodiments for attaching an ear sensor to a concha site;

FIGS. 6A-B are perspective views of a clear adhesive disk embodiment for attaching an ear sensor to a concha site;

FIGS. 7A-C are perspective views of a flexible magnet disk embodiment for attaching an ear sensor to a concha site;

FIGS. 8A-B illustrate a concha-placed reflective sensor embodiment;

FIGS. 9A-B illustrate an "in-the-canal" reflective sensor embodiment;

FIGS. 10A-B illustrate "behind-the-ear" transmissive and/or reflective sensor embodiments;

FIGS. 11A-B illustrate an integrated ear lobe attachment and concha-placed sensor embodiment;

FIGS. 12A-F illustrate a "Y"-clip sensor embodiment for concha-placement;

FIGS. 13A-F, 14A-B, 15A-B, and 16 illustrate various ear sensor attachment support embodiments;

FIGS. 13A-F are side views of ear-hook support embodiments;

FIGS. 14A-B are perspective views of headband support embodiments;

FIGS. 15A-B are front and perspective views of a "stethoscope" support embodiment;

FIG. 16 is a perspective view of a "headphone" support embodiment;

FIGS. 17A-B, 18A-E, 19, 20A-B, 21A-B, 22A-B, 23A-B, 24A-C, 25A-E, 26A-F, and 27A-F illustrate a concha-clip sensor embodiment having an orthogonally-routed sensor cable;

FIGS. 17A-B are perspective views of a concha-clip sensor;

FIGS. 18A-E are top, perspective, front, detector-side and emitter-side views, respectively, of a concha-clip sensor body;

FIG. 19 is an exploded view of an concha-clip sensor;

FIGS. 20A-B are assembly and detailed assembly views of a concha-clip sensor;

FIG. 21A-B are a mechanical representation and a corresponding electrical (schematic) representation of a concha-clip sensor having a DB9 connector;

FIG. 22A-B are a mechanical representation and a corresponding electrical (schematic) representation of a concha-clip sensor having a MC8 connector;

FIG. 23A-B are a mechanical representation and a corresponding electrical (schematic) representation of a concha-clip sensor having a M15 connector;

FIGS. 24A-C are assembly step representations for installing an optical assembly into a resilient frame and installing the resilient frame into a sensor housing;

FIGS. 25A-E are top, perspective, front, side cross-section; and side views, respectively, of a force adjustment ring;

FIGS. 26A-F are top, disassembled perspective, assembled perspective, front, detector-side and emitter-side views of a concha-clip sensor body and corresponding force adjustment ring; and FIGS. 27A-F are top, bottom, perspective, detector-side, front, emitter side and perspective views, respectively of an concha-clip sensor body having a parallel-routed sensor cable.

DETAILED DESCRIPTION OF THE PREFERRED EMBODIMENTS

Figure 1:
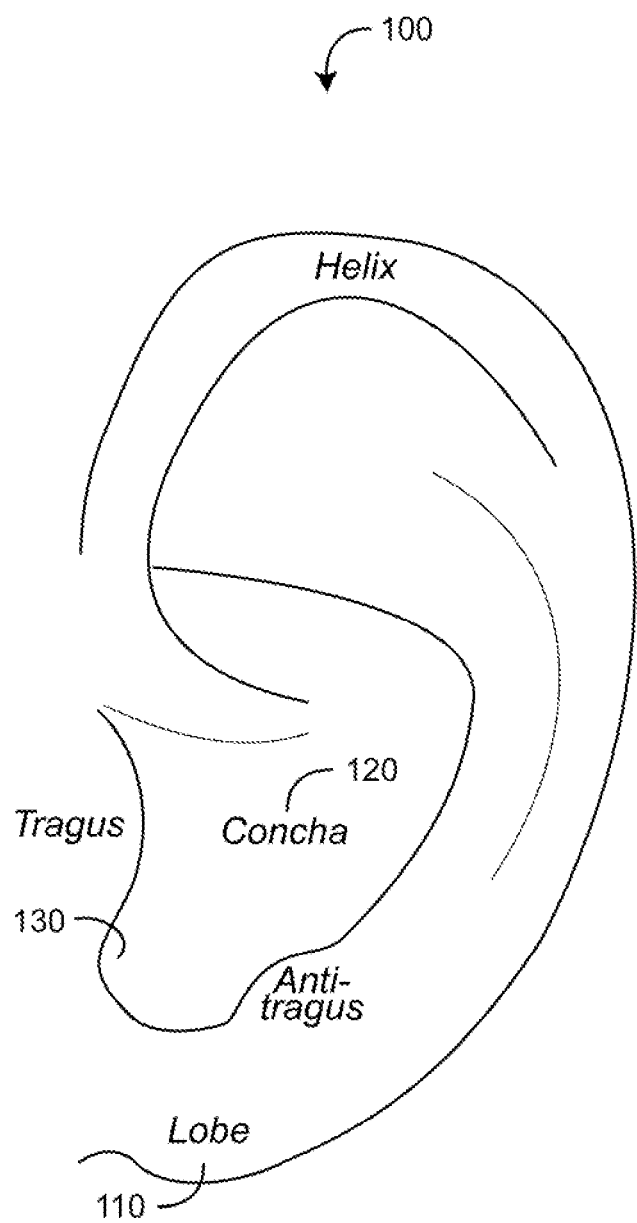
FIG. 1 is an illustration of the pinna or external ear structure, including the concha.
Figure 2A:
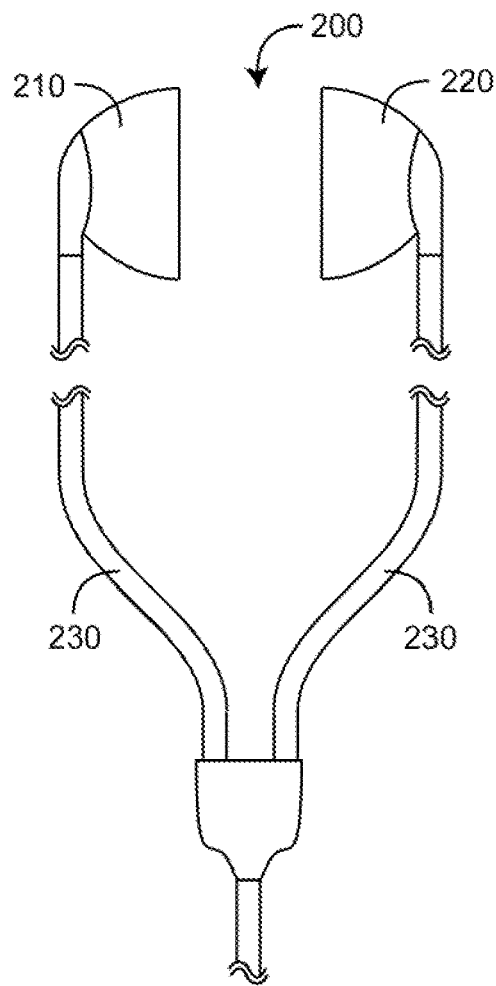
FIGS. 2A-B and 3A-B illustrate various ear sensor embodiments.
Figure 2B:
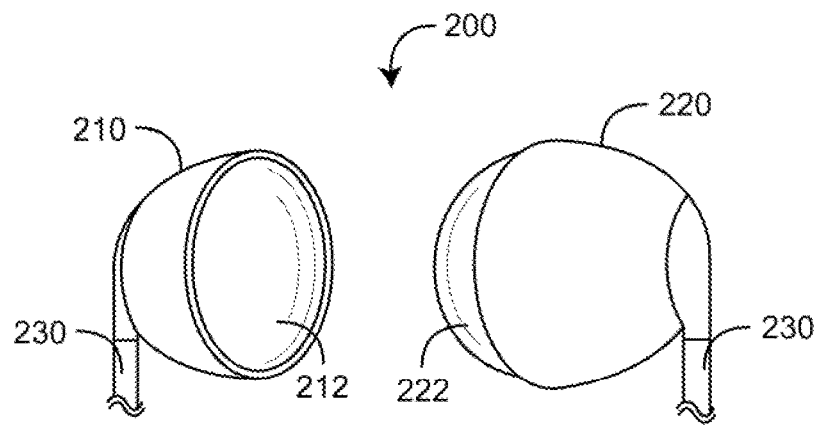

FIGS. 2A-B illustrate an ear bud embodiment of an ear sensor 200 having an emitter ear bud 210, a detector ear bud 220 and connecting cables 230. The emitter ear bud 210 has a generally concave surface for attachment to the back of an ear. The detector ear bud 220 has a generally convex surface 222 for attachment inside the ear at a concha site opposite the emitter ear bud 210. Sensor cables 230 are attached at the back of each ear bud having wires for electrical communications with a physiological monitor, such as a pulse oximeter. In particular, the emitter ear bud 210 includes wires for receiving emitter drive current from a monitor and the detector ear bud 220 includes wires for transmitting photodiode current to the monitor.

Figure 3A:
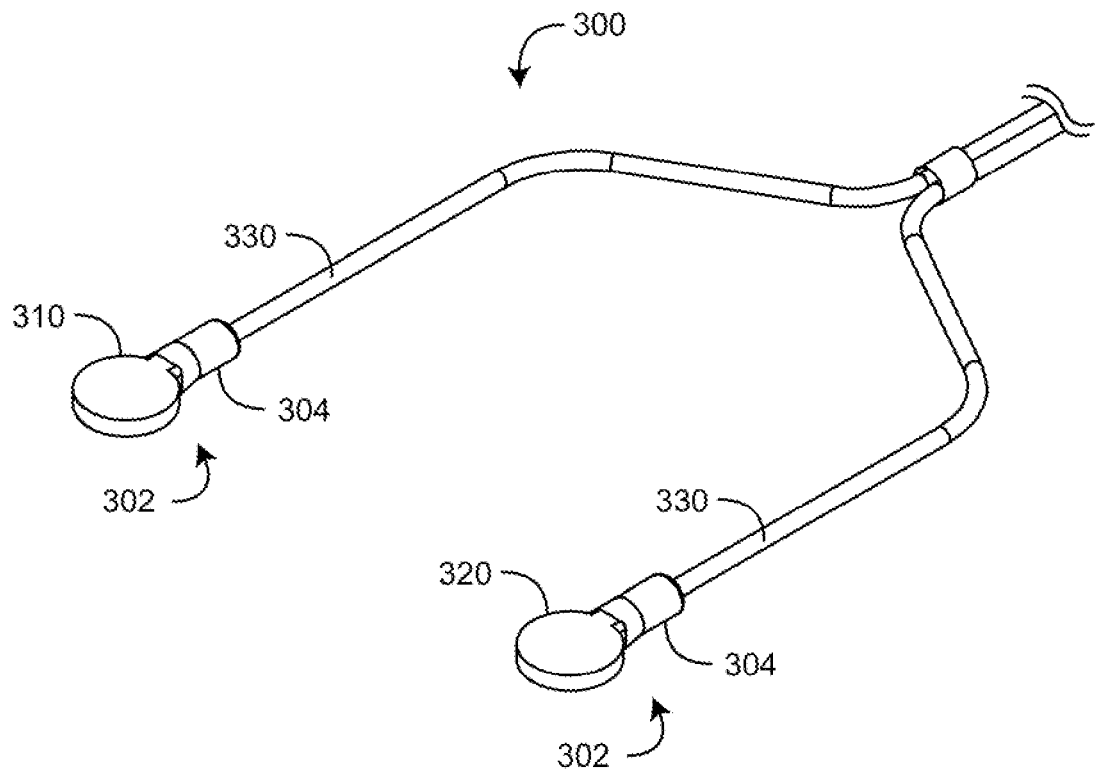
Figure 3B:
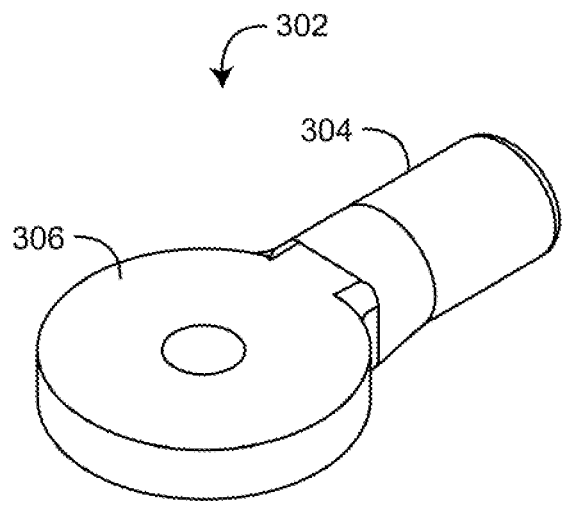

FIGS. 3A-B illustrate a flexible ear pad embodiment of an ear sensor 300 having an emitter pad 310, a detector pad 320 and corresponding cables 330. The sensor pads 310, 320 advantageously include a housing for each of the emitter pad 310 and the detector pad 320, minimizing the number of unique parts for the ear sensor. The detector pad 320 houses a shielded detector assembly (not shown). The emitter pad houses 310 an emitter (not shown). Both the detector pad 320 and the emitter pad 310 are connected to a sensor cable 330. The pads 310, 320 have an integrated bend relief 304 providing a finger grip. The pad face 306 provides a generally planar, pliant contact surface that can adapt to the curved front and back surfaces of a concha site. The pad face 306 has a relatively large area to minimize contact force. The housing 302 is injection molded of a pliant material. In one embodiment, the material is a medical grade thermoplastic elastomer.

FIGS. 2A-B and 3A-B, above, illustrate various ear sensor embodiments. Although described with respect to ear bud and flexible ear pad enclosures, the sensor emitter and detector may be enclosed in any number of housings having various sizes and shapes of ear tissue contact surfaces, may use various types of electrical interconnnect and use various materials so as to noninvasively measure blood parameters from the concha area of the ear. As an example, the detector and emitter may both be mounted at one end of a "Y"-shaped flex circuit that has a connector at the opposite end. Although described above with respect to a detector placed inside the ear and an emitter placed outside the ear, a suitable alternative is the emitter inside and the detector outside the ear. Detector and emitter assemblies are described with respect to FIGS. 19-20, below.

FIGS. 4A-D illustrate "C"-clip embodiments 400 for attaching an ear sensor 410 to a concha site. The clip 400 is adapted for use with either the ear bud or the ear pad embodiments described above. The clip 400 has sensor mounts 420 fixedly attached to each end of a flexible "C"-shaped body 422. The body 422 is made of a suitable material having an appropriate stiffness so as to provide a comfortable yet secure attachment to ear tissue. The sensor mounts 420 have mounting apertures sized for the ear buds or ear pads described above. The ear buds or pads are secured within the apertures with a friction fit or adhesive. In an alternative embodiment, the sensor housings are molded or otherwise integrated with the sensor mounts.

Figure 4A:
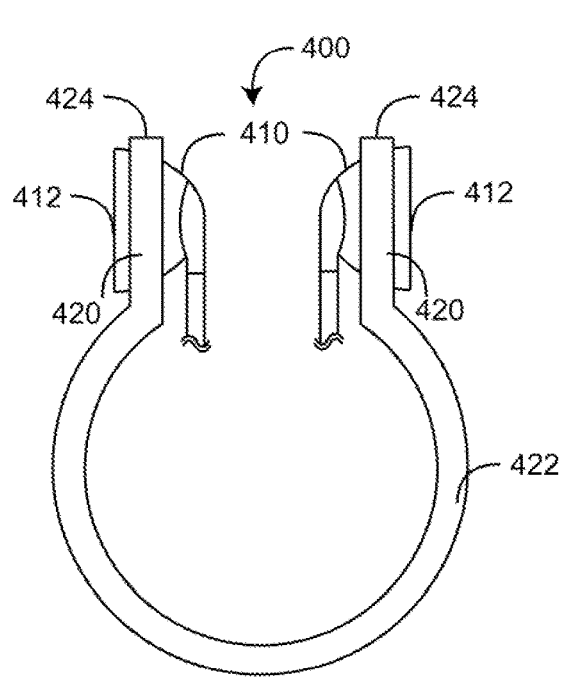
FIGS. 4A-D, 5A-B, 6A-B, and 7A-C illustrate various ear bud/pad attachment embodiments for a concha site.
Figure 4B:
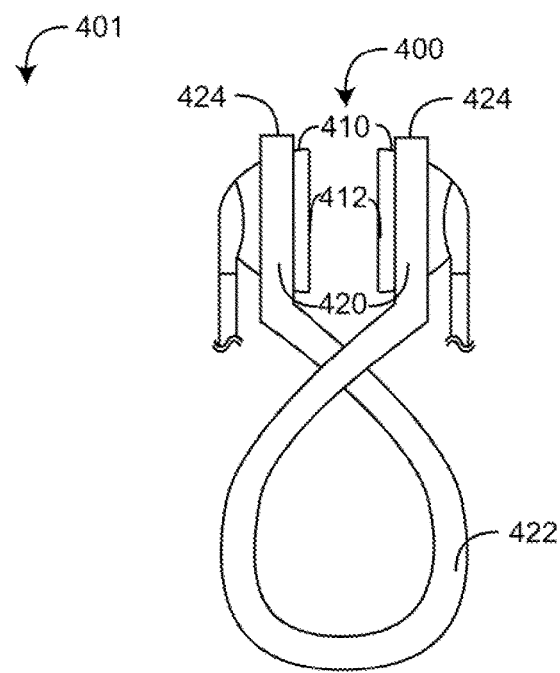
Figure 4C:
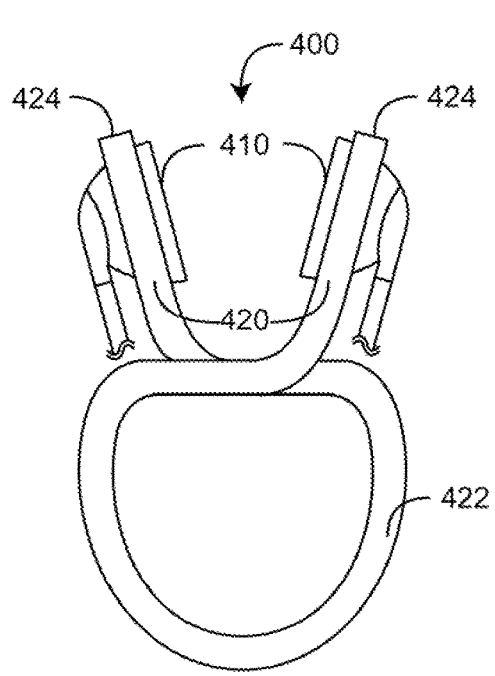
Figure 4D:
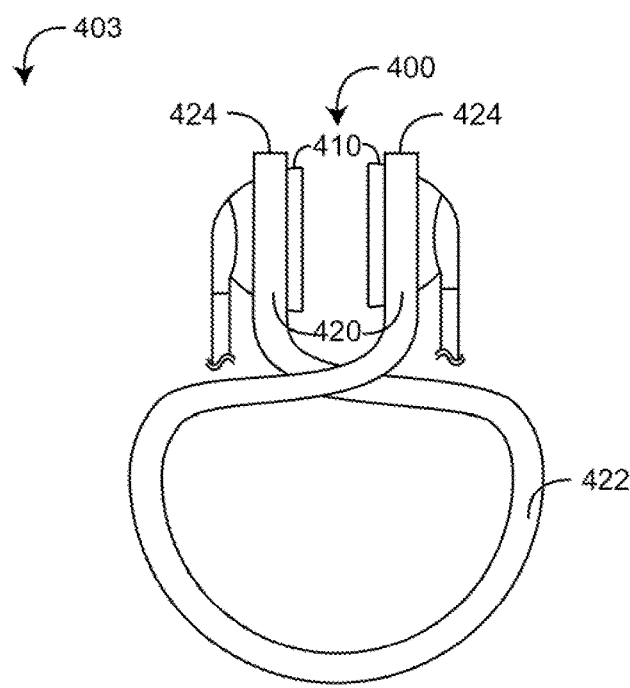

As shown in FIGS. 4A-B, in one embodiment 401 the unflexed clip 400 (FIG. 4A) is compressed between fingertips so that the clip ends 424 are crossed (FIG. 4B) and the contact surfaces of the ear sensor 412 are facing each other. The clip 400 is placed over the ear so that the detector and emitter ear buds are on opposite sides of the ear. Finger pressure on the clip 400 is then released so that the clip tension holds the sensor contact surfaces 412 against the concha tissue. As shown in FIGS. 4C-D, in another embodiment 403 the clip ends 424 are crossed in both the flexed position (FIG. 4C) and the unflexed position (FIG. 4D). Otherwise, sensor attachment is as described above. Although described above as a "C"-shape, the clip body can be constructed of any of various springy, pre-formed materials having a variety of shapes and sizes so as to attach to ear tissue via compression and release between finger and thumb.

Figure 5A:
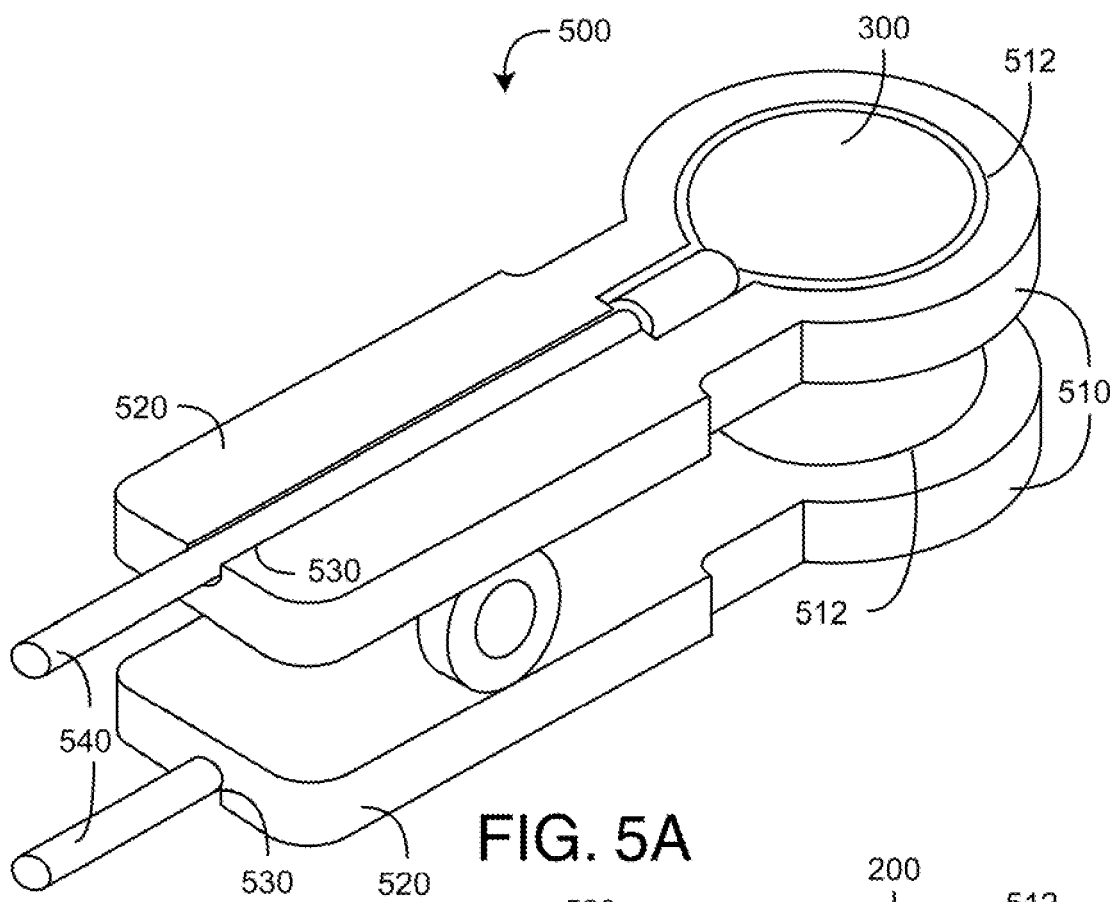
Figure 5B:
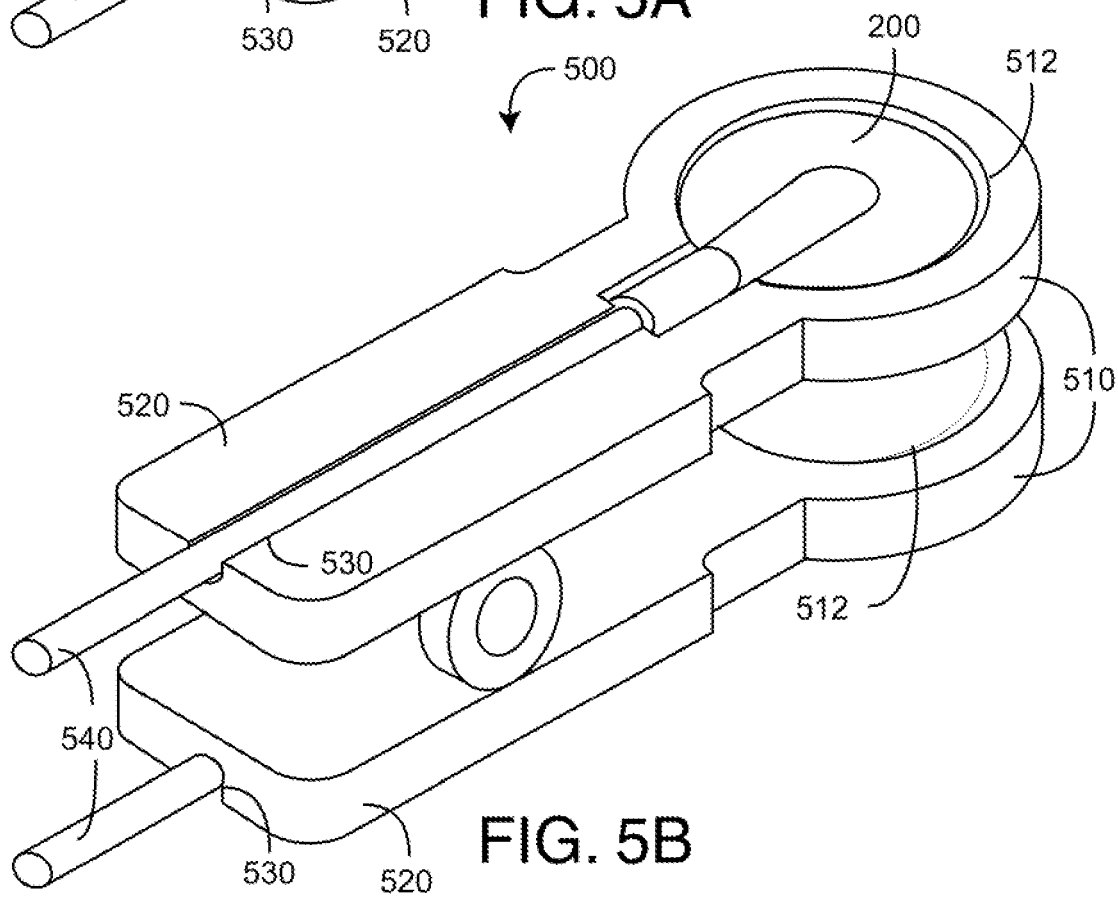

FIGS. 5A-B illustrate an alligator clip embodiment for attaching an ear sensor to a concha site. The alligator clip 500 has opposing heads 510, each with a thru-hole 512 sized to accommodate either an ear pad sensor 300 (FIG. 5A) or an ear bud sensor 200 (FIG. 5B). The alligator clip 500 also has finger grips 520 each with a channel 530 for routing the sensor cabling 540. The alligator clip is compressed and released to position and then attach the corresponding ear sensor to a concha site.

Figure 6A:
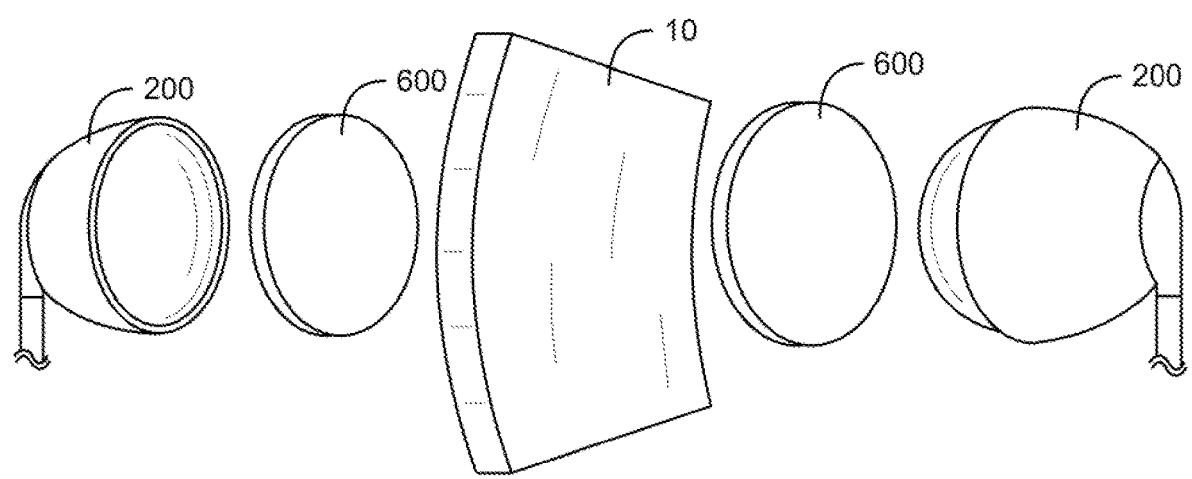
Figure 6B:
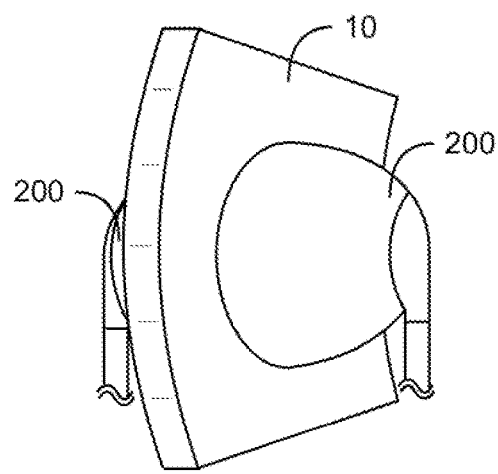

FIGS. 6A-B illustrate an adhesive disk embodiment for attaching an ear sensor to a concha site. Clear disks 600 have an adhesive on both surfaces. The adhesive is bio-compatible on at least the tissue-facing surface. The disks 600 are first attached to the sensor 200 or to a concha site 10. Then the ear sensor 200 is attached on opposite sides of the concha tissue 10. The disks 600 are sized to accommodate either an ear bud sensor 200, as shown, or an ear pad sensor 300 (FIGS. 3A-B).

Figure 7A:
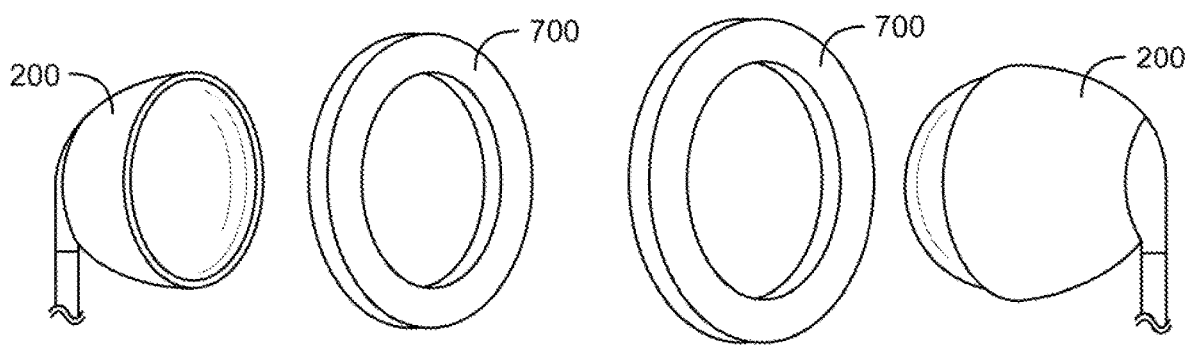
Figure 7B:
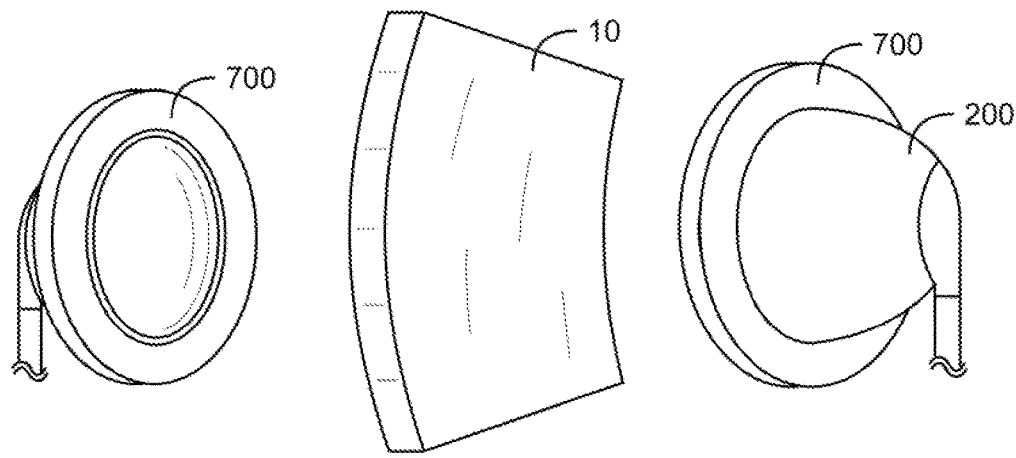
Figure 7C:
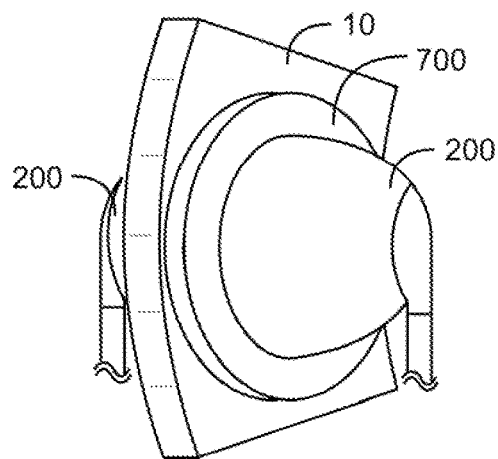

FIGS. 7A-C illustrate a flexible magnet disk embodiment for attaching an ear sensor to a concha site. Flexible magnetic disks 700, such as made from a mixture of a ferrite powder and a rubber polymer resin, are permanently or temporarily attached to an ear sensor 200. The attachment may be by friction fit or a removable or permanent adhesive. The ear sensor 200 is then placed on opposite sides of the concha site 10 and held in place by the magnetic force of the disks. One or both disks may be permanently magnetized during manufacture. The disks 700 are sized to accommodate either the ear bud sensor 200, as shown, or the ear pad sensor 300 (FIGS. 3A-B). In an alternative embodiment, each of the ear sensor housings is at least partially composed of a high magnetic permeable material. One or both of the housings are magnetized. In another embodiment, one or more rare earth magnets are embedded in one or both housings.

FIGS. 4A-D, 5A-B, 6A-B, and 7A-C, described above, illustrate various ear sensor attachment embodiments. Although described with respect to clips and adhesive or magnetic disks, the sensor emitter and detector may be attached to an ear tissue site using various other materials and mechanisms. For example, ear buds or pads may attach via suction cups or disks. Also, an emitter and detector may be integrated with disposable adhesive pads configured with snaps or other mechanical connectors for attaching and removing sensor leads from the disposable pads. In another embodiment, a sensor may be mounted in the concha or the ear canal using an expanding foam material that is first squeezed and then released after sensor placement within the ear.

Figure 8A:
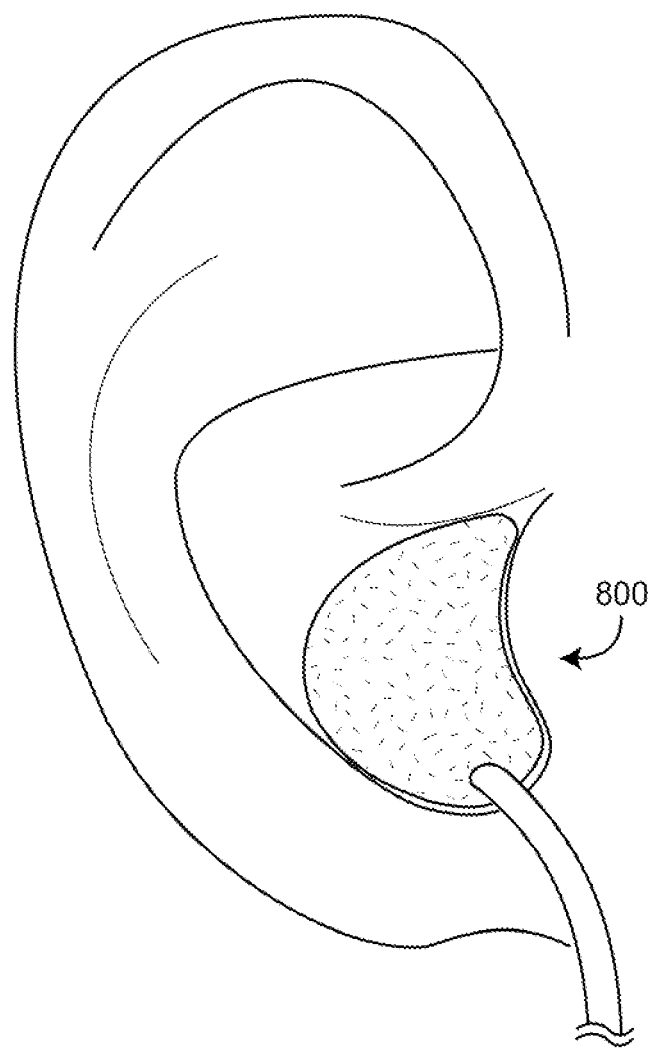
FIGS. 8A-B, 9A-B, and 10A-B illustrate various "hearing aid" style ear sensor embodiments that integrate the ear sensor with an attachment mechanism.
Figure 8B:
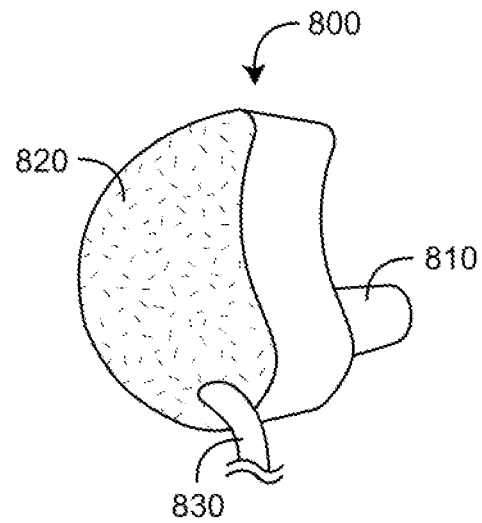

FIGS. 8A-B illustrate a concha-placed reflective sensor embodiment. In one embodiment the sensor 800 has an ear canal extension 810 (FIG. 8B). In an embodiment, the ear canal extension has at least one emitter and at least one detector disposed proximate the extension surface so as to transmit light into ear canal tissue and to detect the transmitted light after attenuation by pulsatile blood flow within the ear canal tissue. In an embodiment, the emitter and detector are axially spaced on the extension. In an embodiment, the emitter and detector are radially spaced on the extension at a fixed angle, which may be, as examples, 30, 45, 90, 120, 135, 160 or 180 degrees.

In an embodiment, the concha-placed sensor body 820 has at least one emitter and at least one detector in lieu of an ear canal extension emitter and detector. The sensor body emitter and detector are disposed proximate the concha surface so as to transmit light into concha tissue and to detect the transmitted light after attenuation by pulsatile blood flow within the concha tissue. In an embodiment, the concha-placed sensor body 820 and the ear canal extension 810 both have at least one emitter and at least one detector, creating a multi-site (concha and ear canal) reflective sensor. Connected with the sensor body 820 is a sensor cable 830 providing electrical communications between sensor body/ear canal emitter(s) and detector(s) and a monitor. Detector and emitter assemblies are described with respect to FIGS. 19-20, below.

Figure 9A:
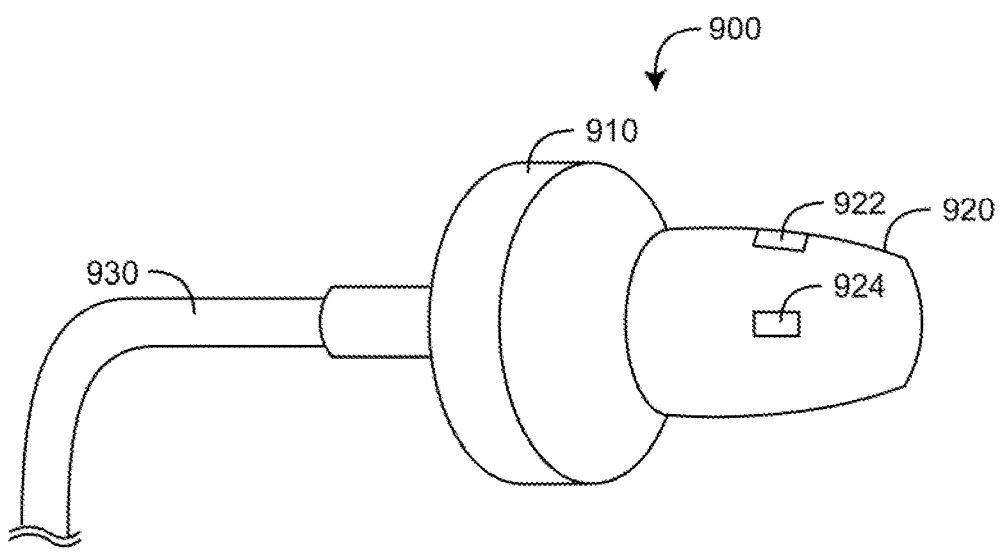
Figure 9B:
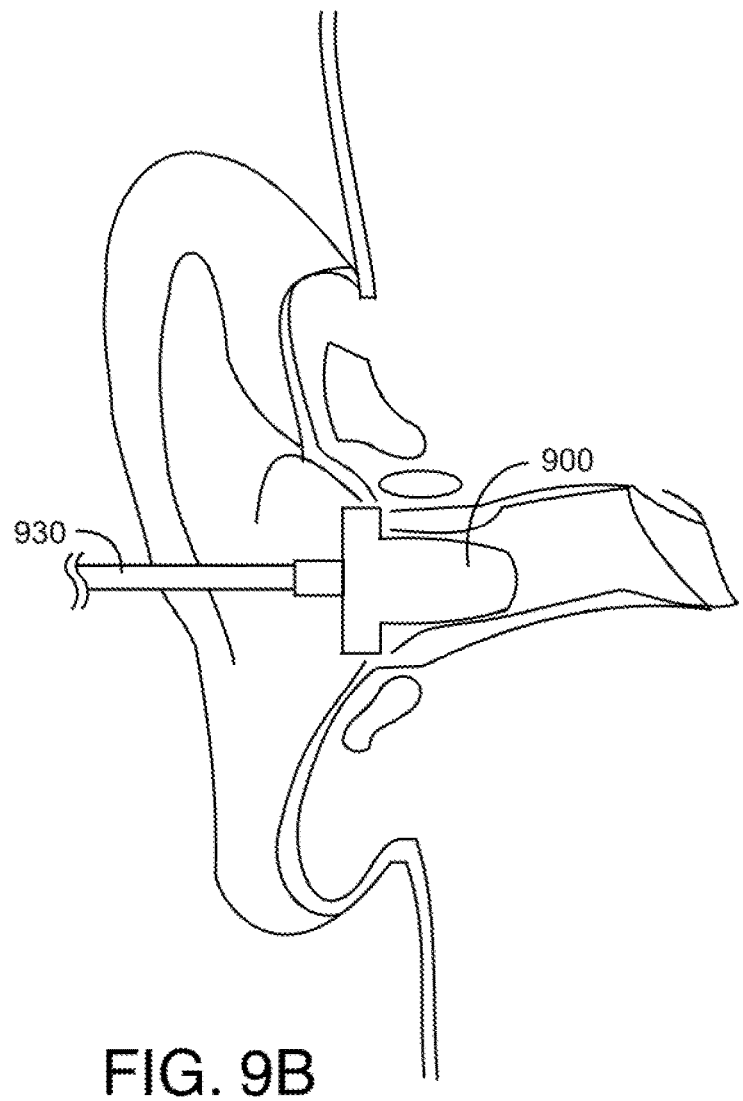

FIGS. 9A-B illustrate an "in-the-canal" ear sensor embodiment. The ear canal sensor 900 has a base 910, an ear canal extension 920 and a sensor cable 930. Similar to the embodiment described above, the ear canal extension 920 has at least one emitter 922 and at least one detector 924 disposed proximate the extension surface so as to transmit light into ear canal tissue and to detect the transmitted light after attenuation by pulsatile blood flow within the ear canal tissue. The emitter 922 and detector 924 may be axially-spaced on the ear canal extension a fixed distance. Alternatively, the emitter and detector may be radially-spaced on the ear canal extension at any of various angles, such as 30, 45, 90, 120, 135, 160 or 180 degrees, to name a few. A sensor cable 930 is attached to the sensor so as to extend from the ear canal to a corresponding monitor.

Figure 10A:
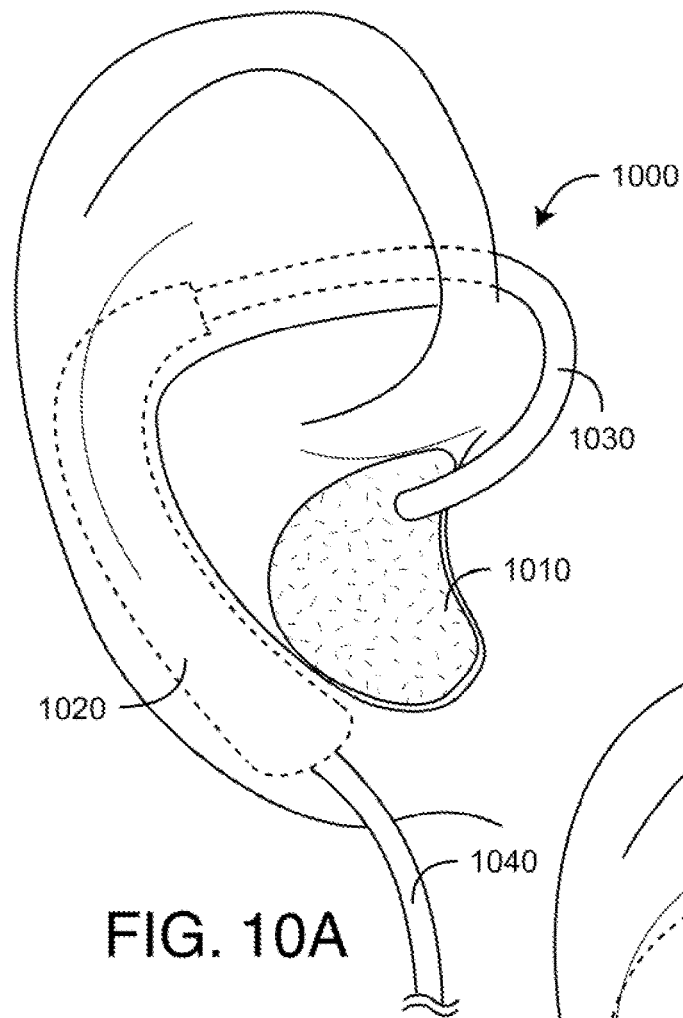
Figure 10B:
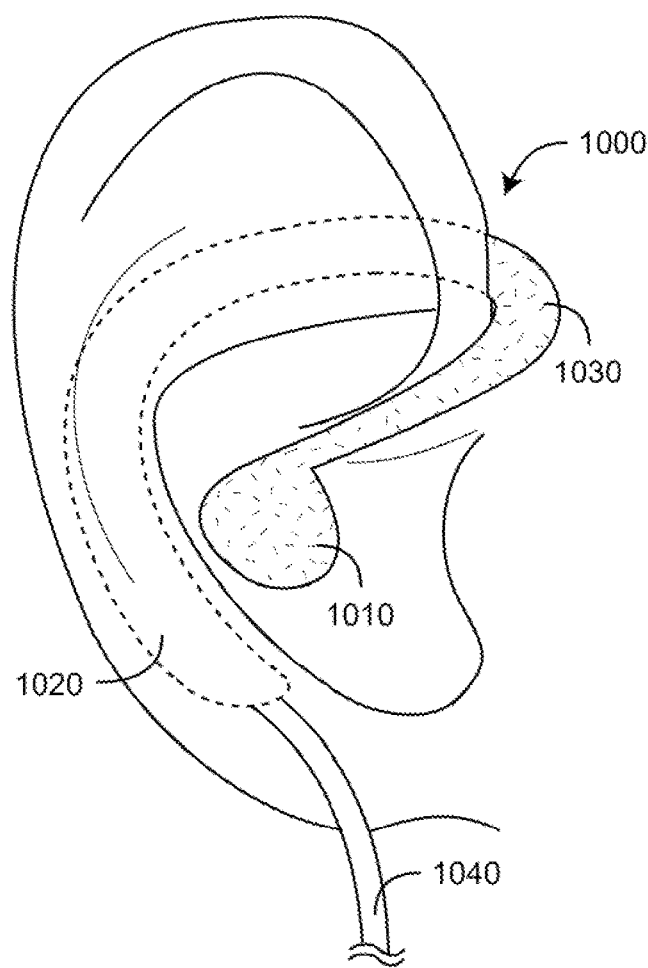

FIGS. 10A-B illustrate "behind-the-ear" transmissive and/or reflective sensor embodiments. The ear sensor 1000 has a concha-placed body 1010, an ear piece 1020, a connecting piece 1030 attaching the concha body 1010 and the ear piece 1020 and a sensor cable 1040. In one embodiment, a concha-placed body 1010 houses a detector and the ear piece 1020 houses an emitter opposite the detector so as to configure a transmissive concha sensor. In an embodiment, the concha-placed body 1010 or the ear piece 1020 has both an emitter and a detector so as to configure a reflective concha sensor. In an embodiment, the concha body 1010 and the ear piece 1020 are configured for multi-site transmissive and/or reflective concha tissue measurements. In an embodiment, the concha body 1010 also has an ear canal extension (see, e.g. 810 FIG. 8B), which may also have an emitter and detector for multi-site concha and ear canal measurements. A sensor cable 1040 extends from the ear piece 1020 as shown. Alternatively, a sensor cable extends from the concha body, such as shown in FIG. 8B, above.

Figures 11A, 11B:
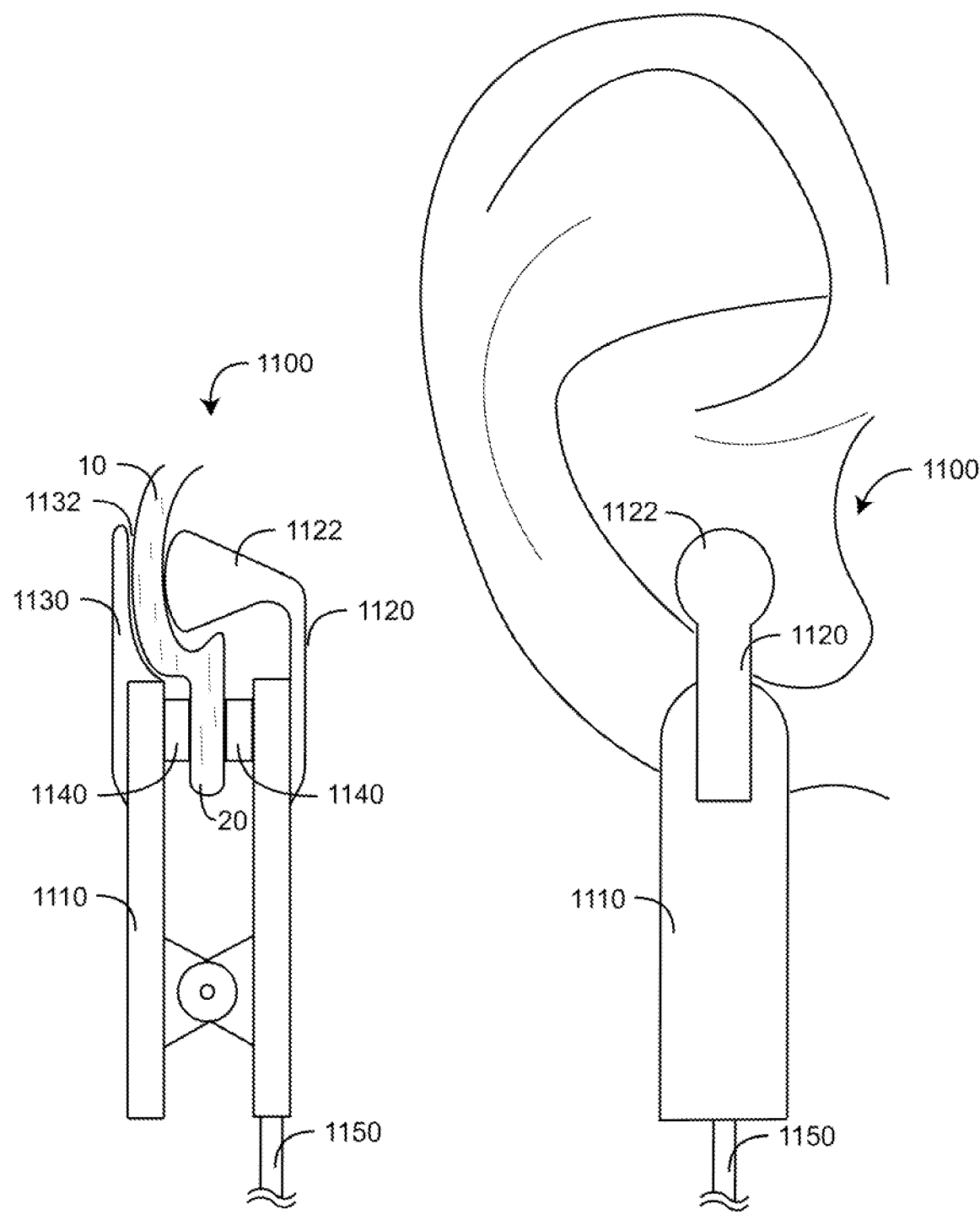
FIGS. 11A-B and 12A-F illustrate additional integrated ear sensor and attachment embodiments.
Figure 12A:
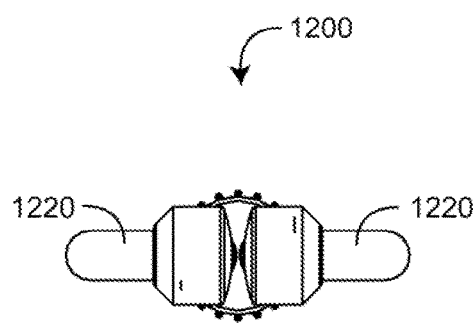
Figure 12B:
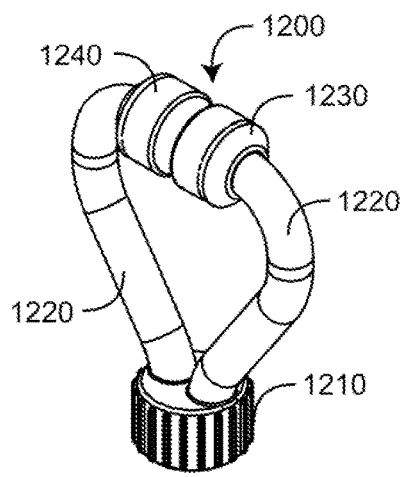
Figure 12C:
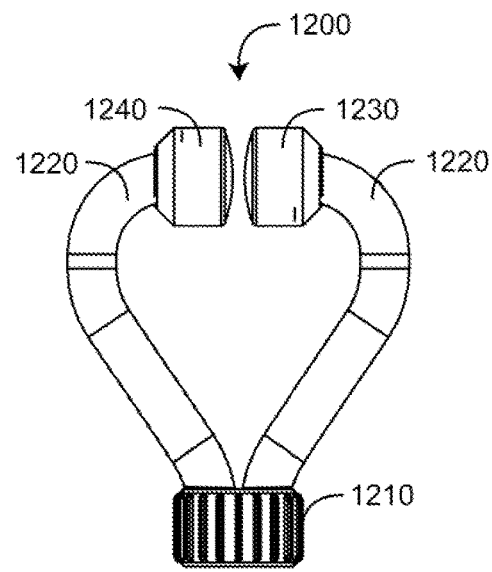
Figure 12D:
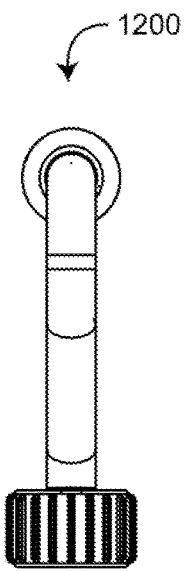
Figure 12E:
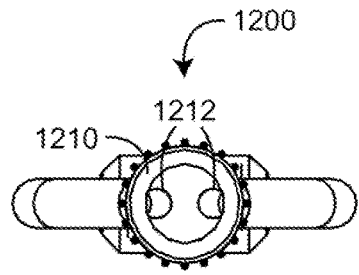
Figure 12F:
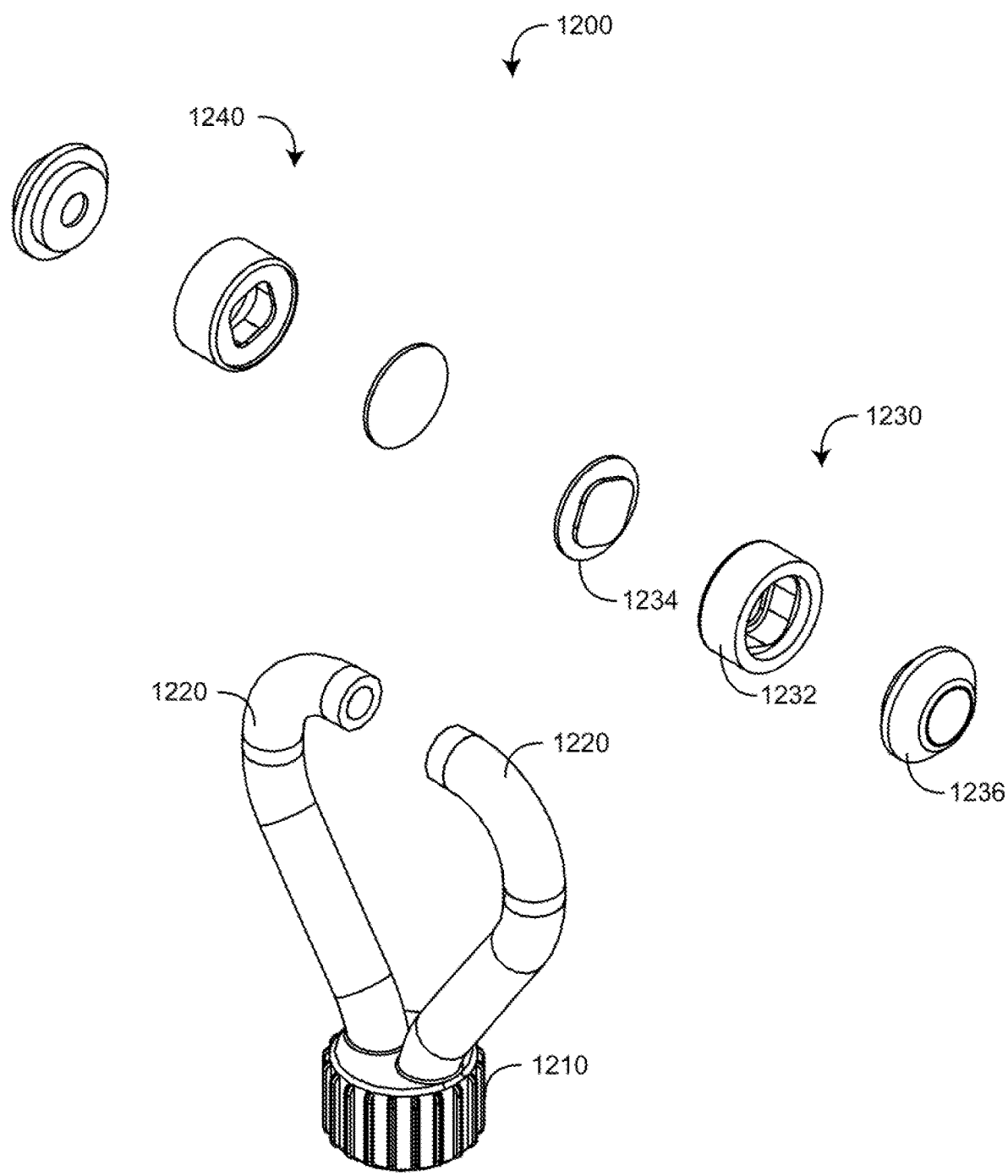
Figure 13A:
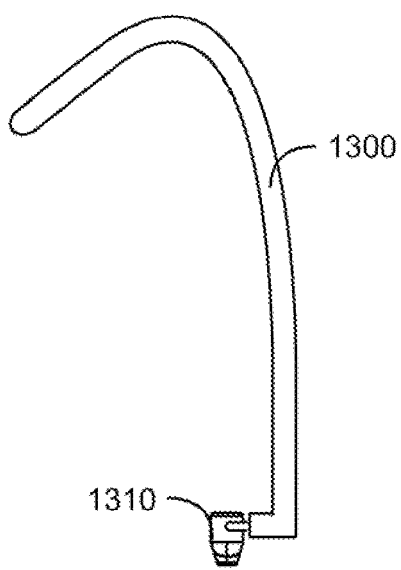
Figure 13B:
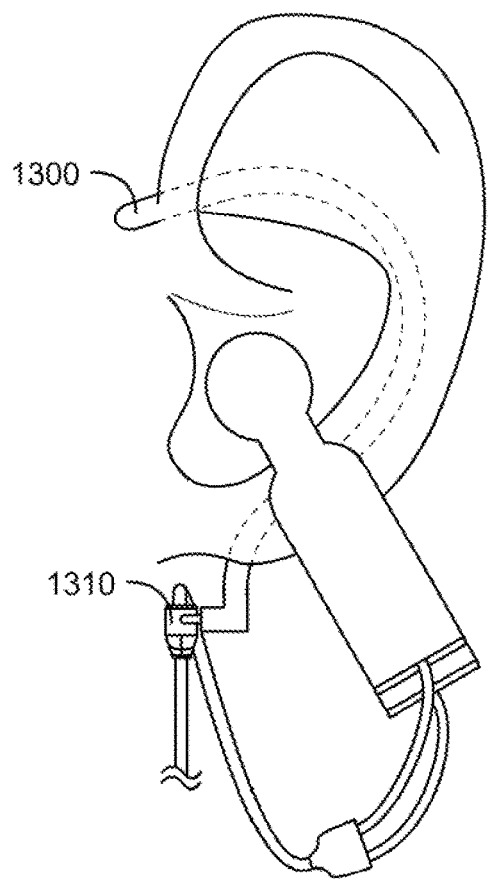
Figure 13C:
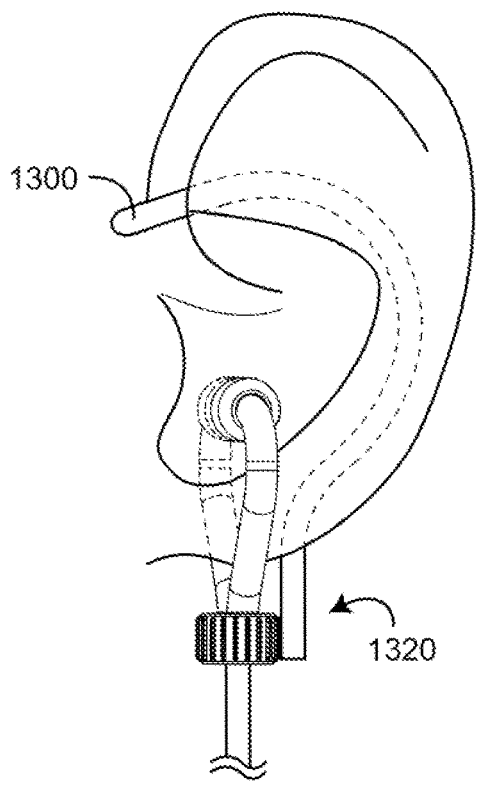

FIGS. 11A-B illustrate a concha sensor 1100 having an alligator clip 1110, a concha piece 1120, a ear back piece 1130, a lobe attachment 1140 and a sensor cable 1150. In an embodiment, the alligator clip 1110 attaches to the ear lobe 20 so as to provide the physical support for a concha sensor 1100. A convex body 1122 extends from the concha piece 1120. A detector disposed at the convex body 1122 surface is disposed against the concha tissue 10. A concave surface 1132 is defined on the back piece 1130 and positioned behind the ear. An emitter disposed at the concave surface 1132 is disposed against the ear wall opposite the concha detector. The concha piece 1120 and ear back piece 1130 are "springy" so as to securely contact the concha tissue 10 under the force of the alligator clip 1110, but without undue discomfort. In an embodiment, the lobe attachment 1140 also has an emitter and detector so as to provide multi-site ear tissue measurements at the ear lobe 20 and the concha 10.

FIGS. 12A-F illustrate a "Y"-clip ear sensor 1200 having a base 1210, a pair of curved clips 1220 extending from the base, an emitter assembly 1230 extending from one clip end and a detector assembly 1240 extending from another clip end. The clips 1220 are tubular so as to accommodate wires from the emitter/detector assemblies, which extend from apertures 1212 in the base. Each assembly has a pad 1232, a molded lens 1234 and a lid 1236, which accommodate either an emitter subassembly or a detector subassembly. The Y-"clips" flex so as to slide over the ear periphery and onto either side of the concha. The integrated emitter and detector, so placed, can then transmit multiple wavelength light into the concha tissue and detect that light after attenuation by pulsatile blood flow within the concha tissue.

FIGS. 13A-F illustrate ear hook sensor support embodiments having an ear hook 1300 with cable 1310, fixed 1320 or sliding 1330 support for either an alligator clip or a "Y"-clip sensor. These embodiments are also applicable to "C"-clip sensors and alligator clip sensors, among others.

Figure 14A:
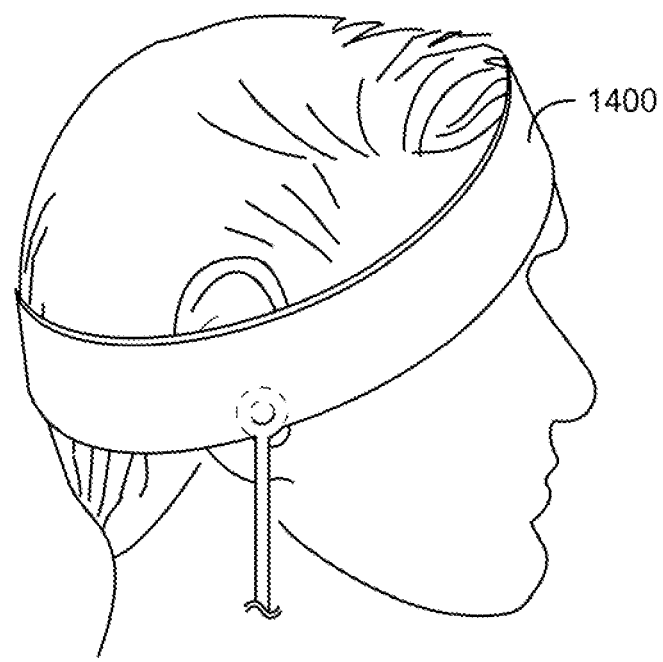
Figure 14B:
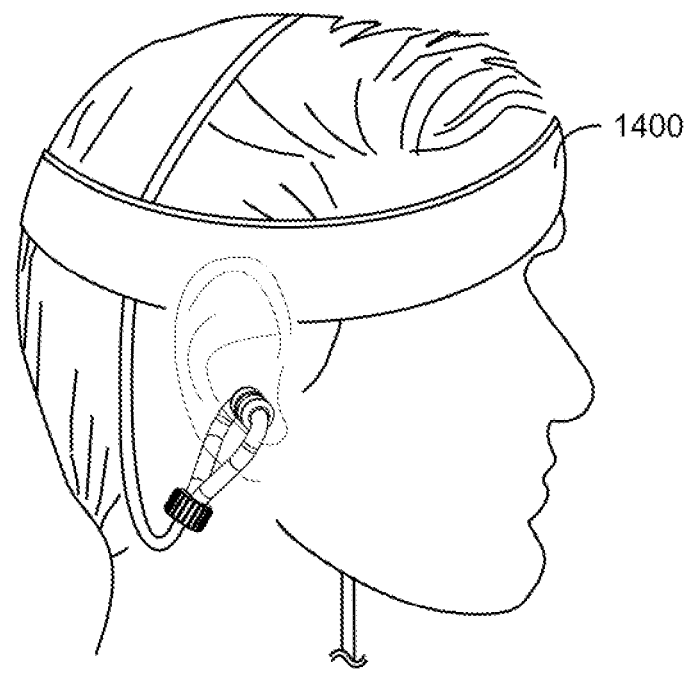

FIGS. 14A-B illustrate headband sensor support embodiments. In one embodiment, the headband 1400 secures a concha body (FIGS. 8A-B) or an ear canal sensor (FIGS. 9A-B) by placement over the ear. In another embodiment, the headband 1400 provides a cable support for an ear clip sensor.

Figure 15A:
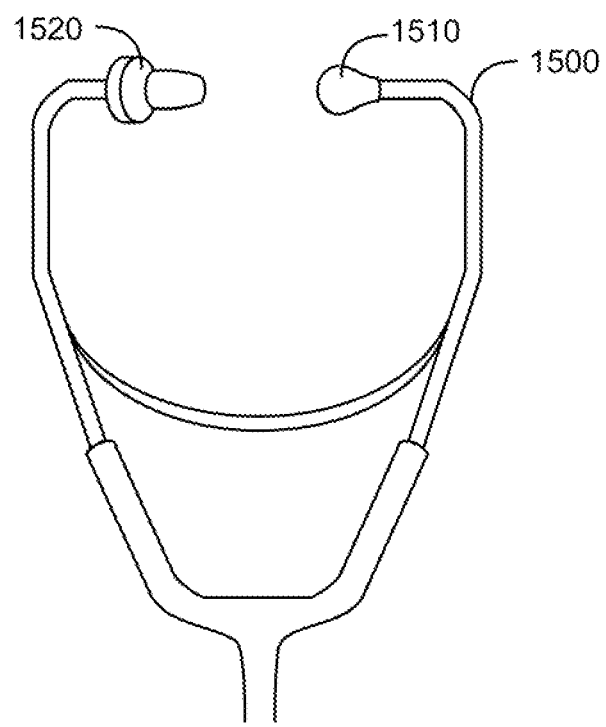
Figure 15B:
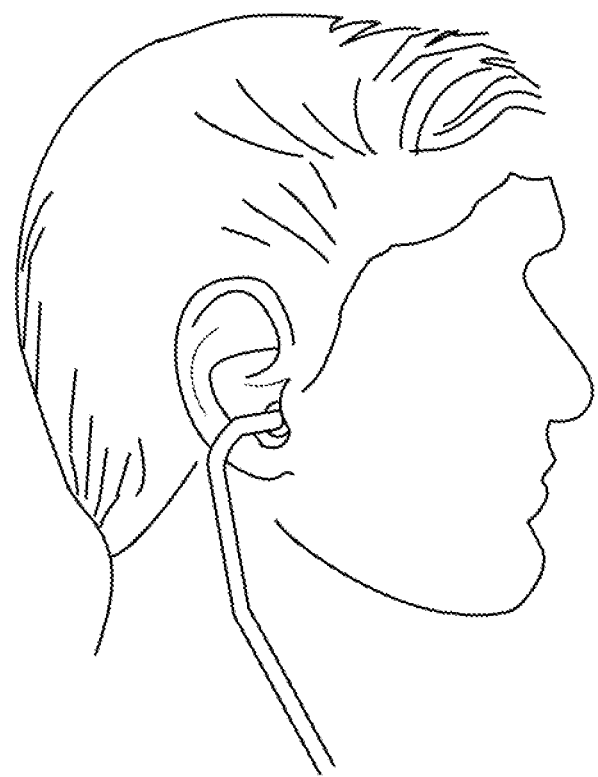

FIGS. 15A-B illustrate a "stethoscope" 1500 sensor support embodiment. In this embodiment, one ear piece 1510 is integrated with an ear canal sensor 1520, such as described above with respect to FIGS. 9A-B. In another embodiment, both stethoscope ear pieces 1510 are integrated with ear canal sensors for multi-site (both ears) blood parameter measurements.

Figure 16:
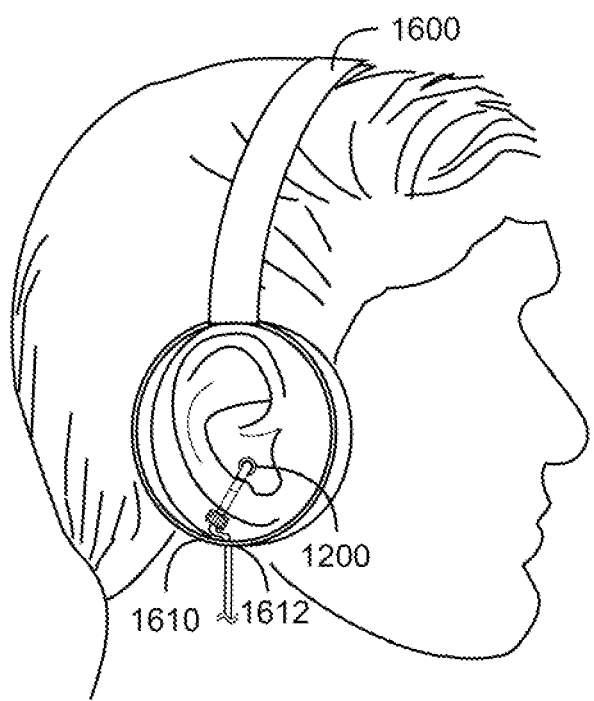

FIG. 16 illustrates a "headphone" 1600 support embodiment. In one embodiment (not shown), a headphone ear piece secures a concha body (FIGS. 8A-B) or an ear canal sensor (FIGS. 9A-B) by placement over the ear, in a similar manner as described with respect to FIGS. 14A-B. In another embodiment, the headphone 1600 provides a "ring-shaped" earpiece 1610 that provides a cable support 1612 for an ear clip sensor 1200, as shown.

Figure 17A:
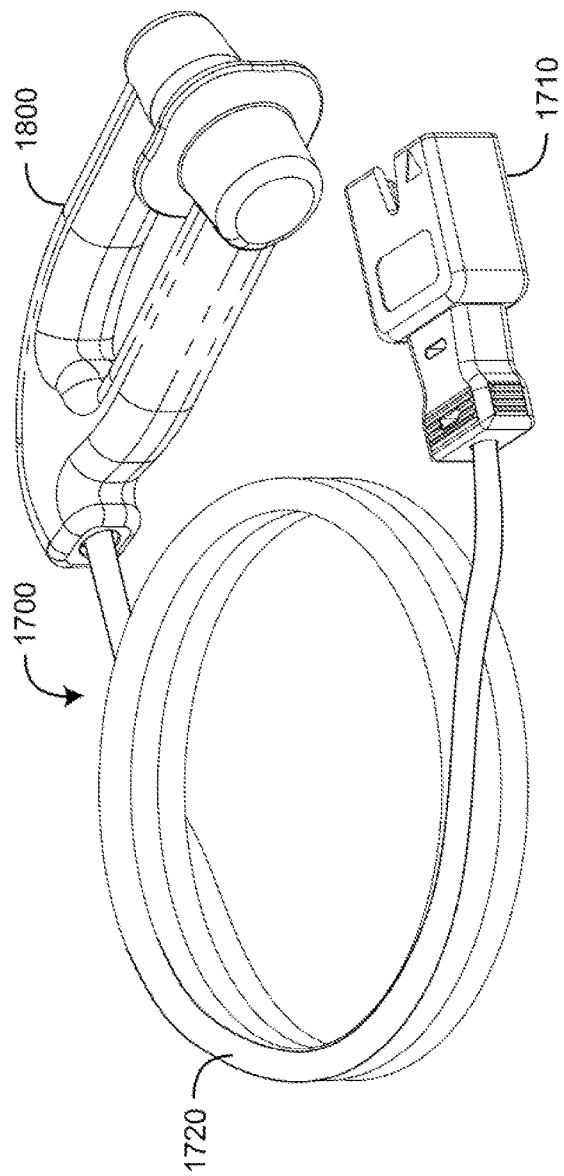
Figure 17B:
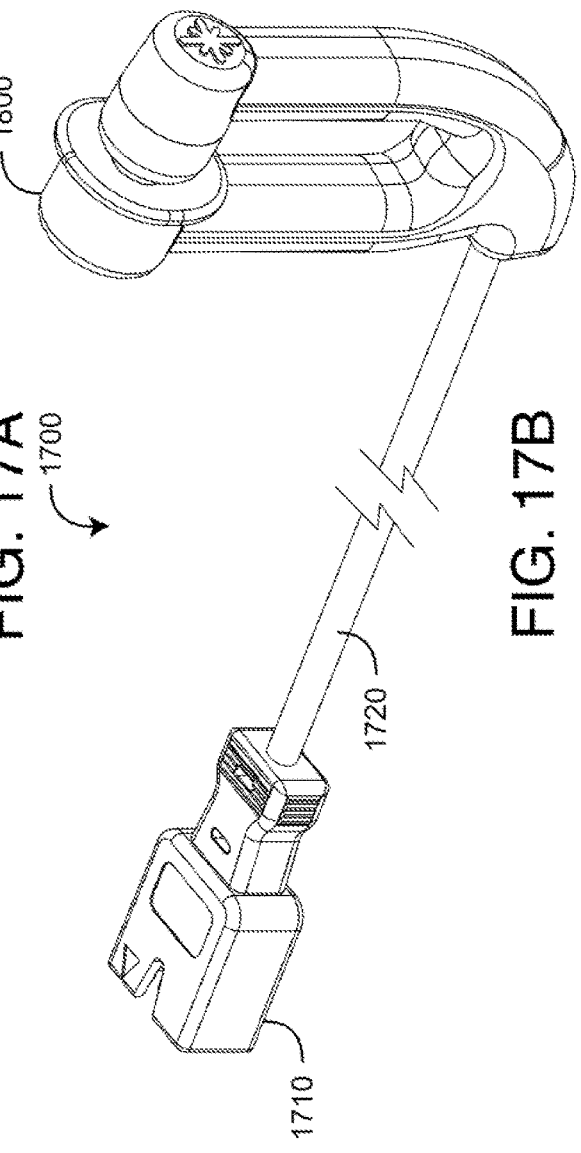
Figure 18B:
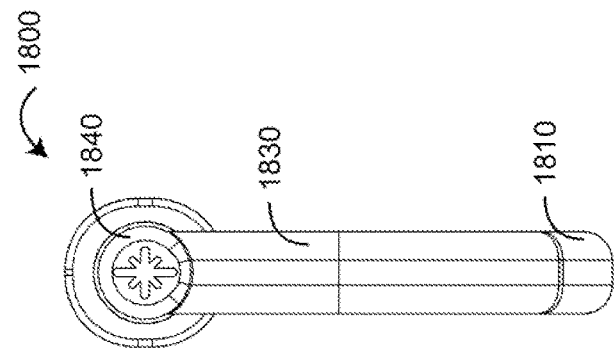
Figure 18E:
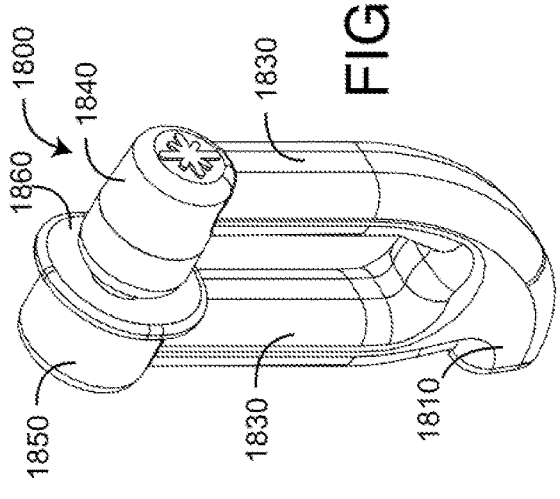
Figure 18D:
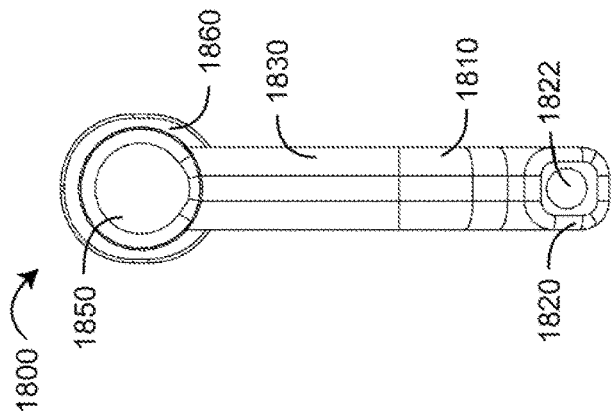
Figure 18A:
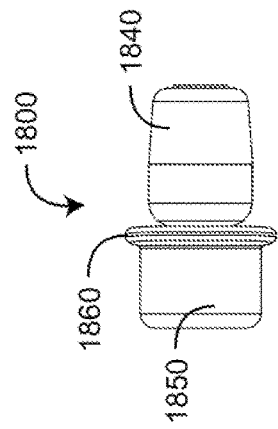
Figure 18C:
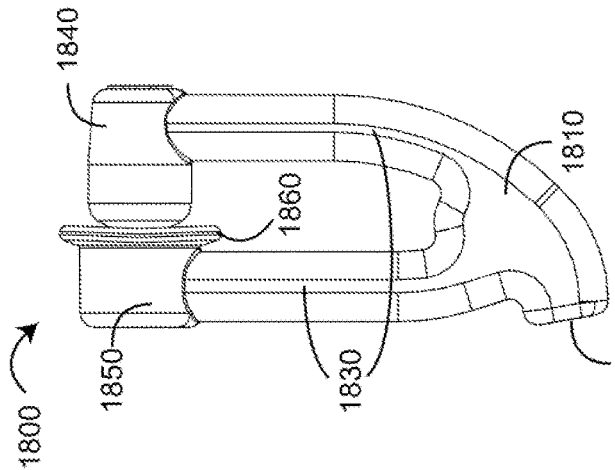

FIGS. 17A-B illustrate a concha-clip ear sensor 1700 embodiment having a sensor body 1800, a connector 1710 and a sensor cable 1720 providing communications between the sensor body 1800 and the connector 1710. As described in further detail with respect to FIGS. 18A-E, the sensor body 1800 has resilient legs that are manually flexed so as to slide over an ear periphery and onto either side of a concha site. As described in further detail with respect to FIG. 19, the sensor body 1800 incorporates an optical assembly 1910 (FIG. 19) configured to transmit multiple wavelength light into the concha tissue and detect that light after attenuation by pulsatile blood flow within the concha tissue. In a particular embodiment, the sensor body 1800 has an emitter housing 1840 (FIGS. 18A-E) configured to fit inside the ear and a detector housing 1850 (FIGS. 18A-E)

configured to fit outside the ear. In other embodiments, the sensor body is configured so as to place an emitter outside the ear and a detector inside the ear. In an embodiment, the sensor body 1800 is configured so that the sensor cable 1720 extends generally perpendicular to the sensor body 1800, as shown and described with respect to FIGS. 17-26. In another sensor body embodiment 2700 (FIGS. 27A-F) the sensor cable 1720 extends generally parallel to the sensor body, as described in further detail with respect to FIGS. 27A-E, below. Although the sensor body 1800, 2700 as described below has legs 1830 extending from a base 1810 so as to generally form a "U"-shape, the sensor body 1800, 2700 can be constructed of any of various resilient, pre-formed materials having a variety of shapes and sizes so as to attach to ear tissue, such as a concha site or ear lobe site.

FIGS. 18A-E further illustrate a sensor body 1800 having a base 1810, a strain relief 1820 formed at a side of the base 1810 and a pair of resilient legs 1830 extending from the base 1810. The strain relief 1820 has a cable aperture 1822 that accommodates the sensor cable 1720 (FIGS. 17A-B). An emitter housing 1840 extends from one leg 1830 and a detector housing 1850 extends from the other leg 1830. The legs 1830 accommodate cable conductors extending between the connector 1710 (FIGS. 17A-B) and an optical assembly 1910 (FIG. 19) located in the housings 1840, 1850. Each housing 1840, 1850 has an optical end 1842, 1852 (FIG. 20B) having an aperture 1844, 1854 (FIG. 20B) that passes light from the emitter housing 1840 to the detector housing 1850. In an embodiment, the housings 1840, 1850 fit on either side of a concha tissue site so that light is transmitted from an emitter 1916 (FIG. 19), through the concha tissue and received by a detector 1912 (FIG. 19), as described in detail below. In an embodiment, the emitter housing 1840 fits within the ear and the detector housing 1850 outside the ear. In an embodiment, a cup 1860 extends from the detector housing 1850. The cup 1860 has a generally circular edge and a curvature that accommodates the surface behind the ear. Accordingly, the cup 1860 advantageously provides a more comfortable and secure fit of the detector housing 1850 to the ear and further functions as a light shield, blocking external light sources from the detector 1912. The resilient legs 1830 are manually flexed so that the emitter housing 1840 is moved away from the detector housing 1850 so as to position the detector housing 1850 and emitter housing 1840 over opposite sides of a concha site. The legs are then released to an unflexed position so that the concha site is grasped between the detector housing 1850 and emitter housing 1840.

Figure 19:
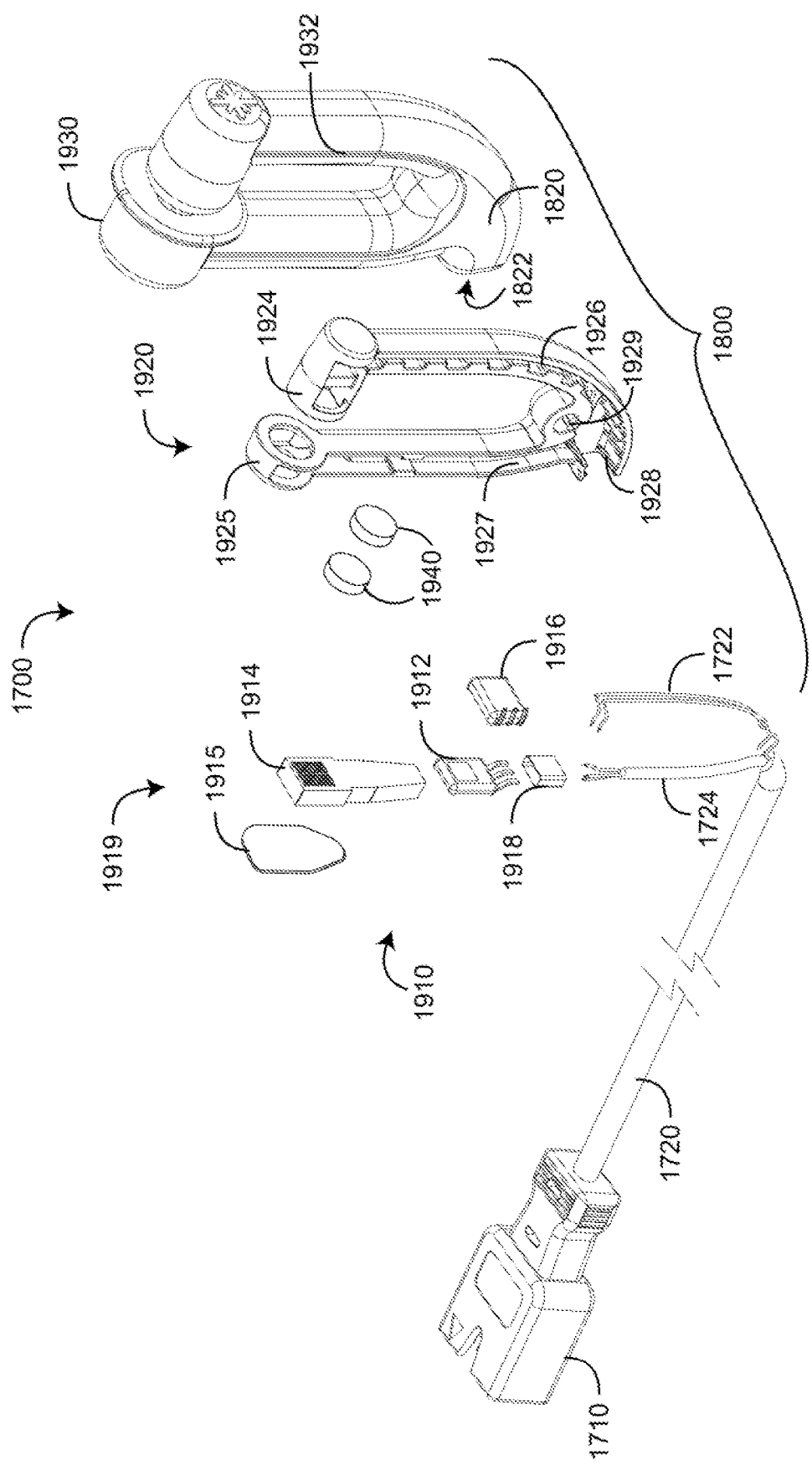
Figures 20A, 20B:
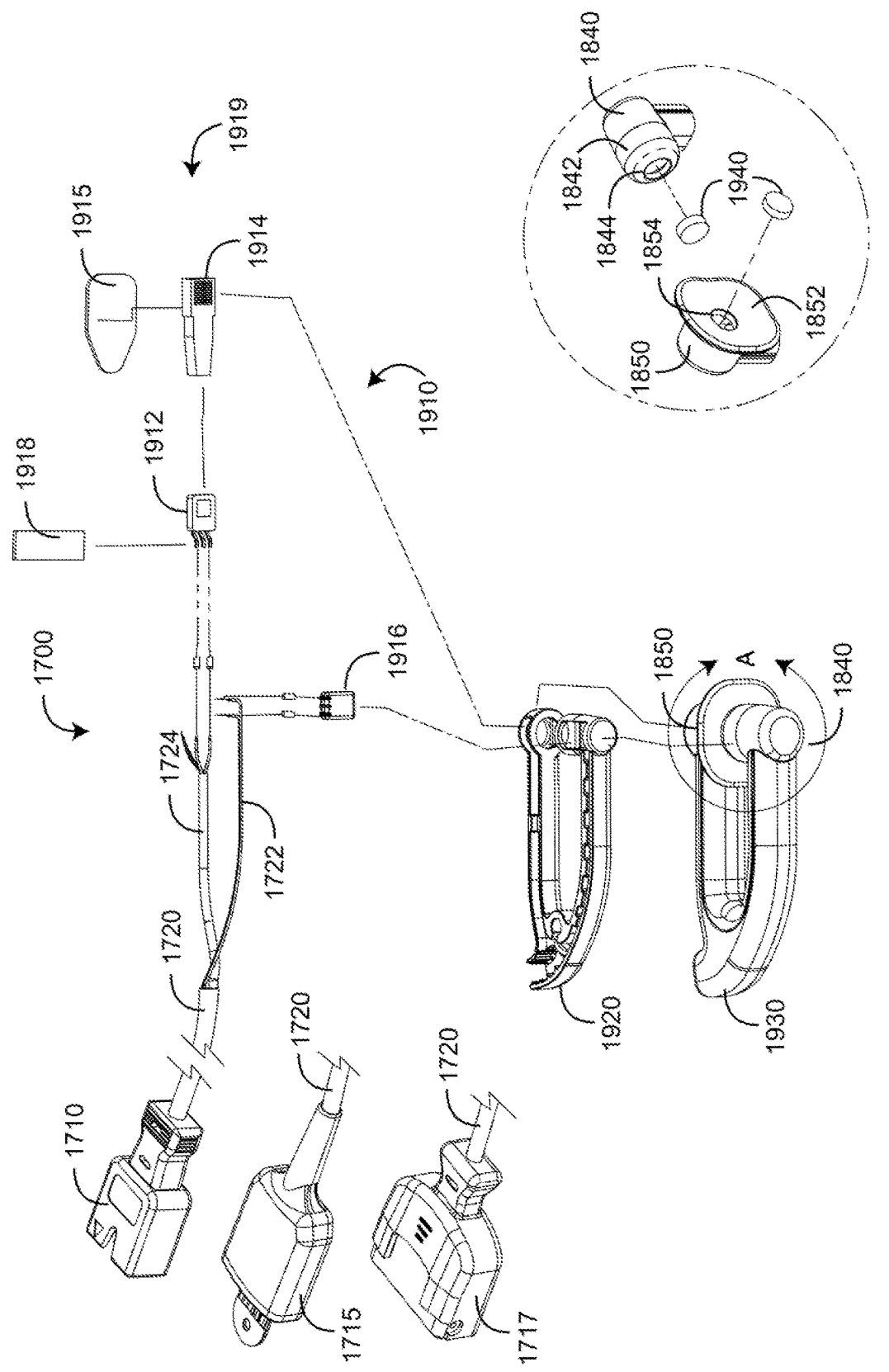
Figure 21A:
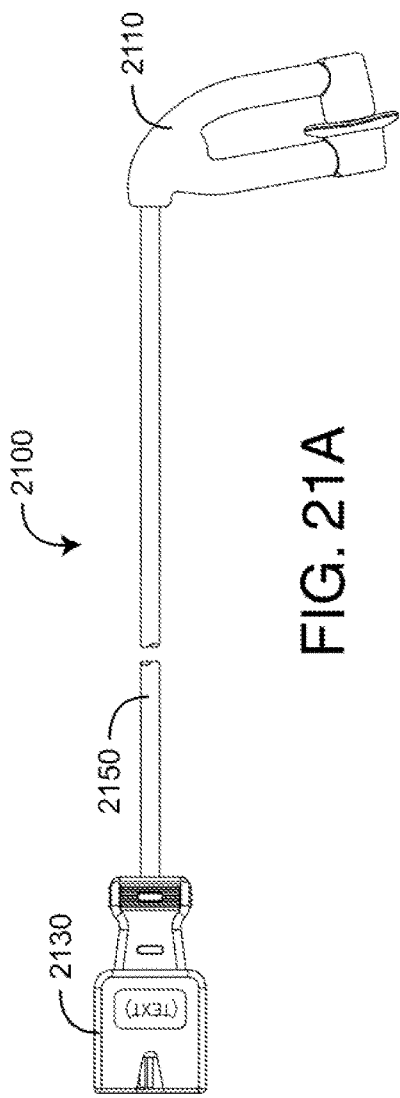
Figure 21B:
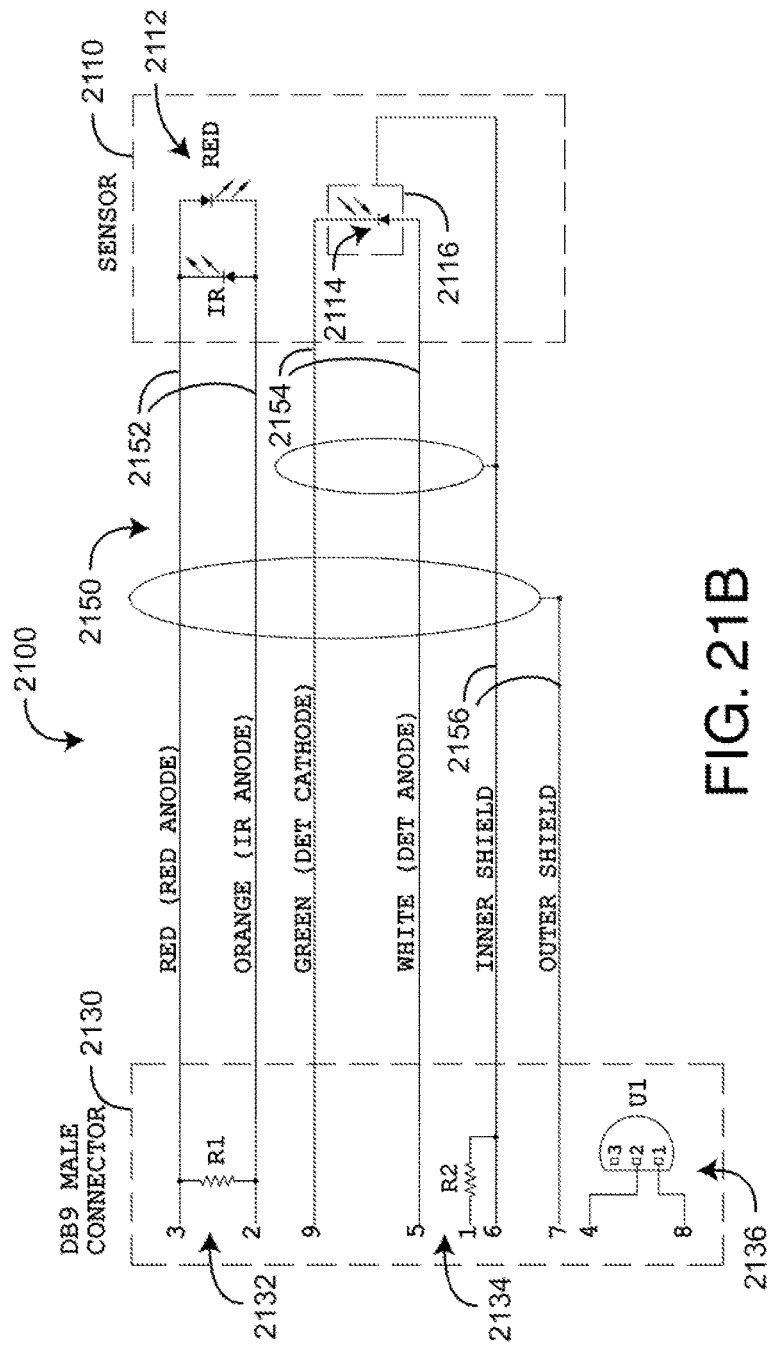
Figure 22A:
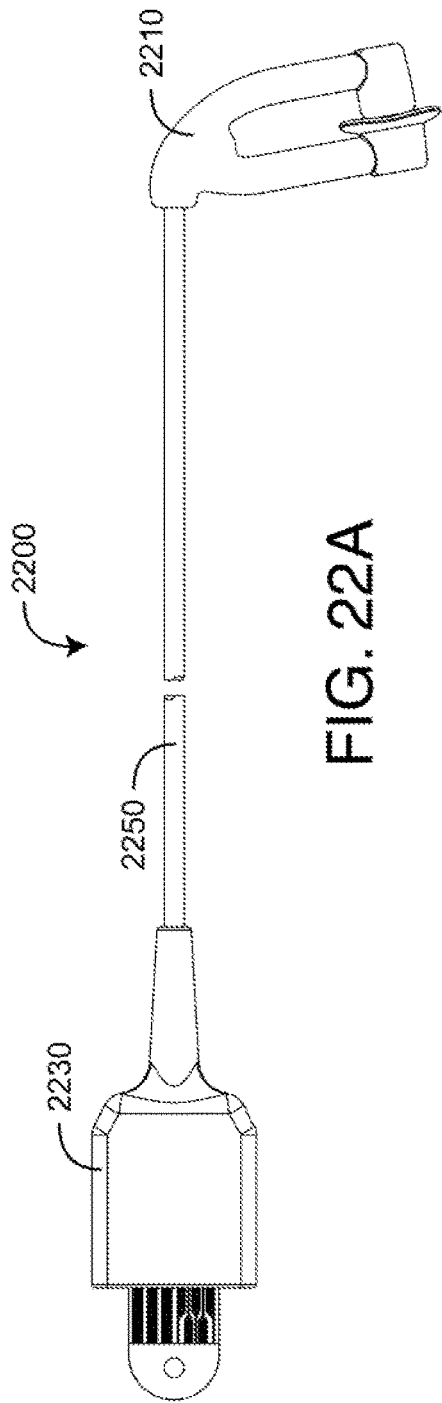
Figure 22B:
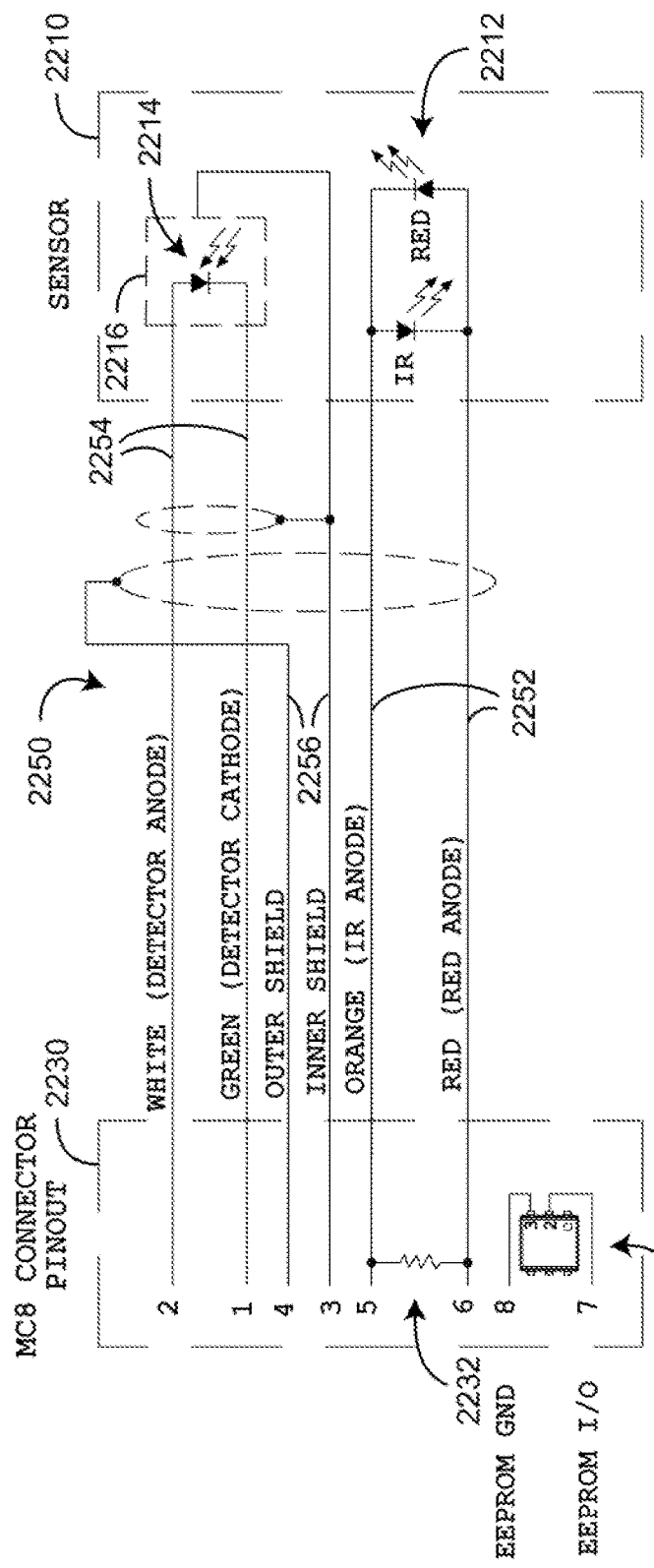

FIGS. 19, 20A-B further illustrates a concha-clip ear sensor 1700 having a connector 1710 in communications with a sensor body 1800 via a sensor cable 1720. The sensor body 1800 has an optical assembly 1910, a resilient frame 1920, a sensor housing 1930 and lenses 1940. As shown in FIGS. 19-20, the optical assembly 1910 has a detector 1912, a detector shield 1914, a light barrier 1915, an emitter 1916 and white electrical tape 1918. The cable 1720 has emitter wires 1722 and detector wires 1724 that are soldered to the emitter 1916 and detector 1912, respectively, and communicate emitter drive signals and detector response signals to/from the connector 1710.

Also shown in FIGS. 19, 20A-B, the resilient frame 1920 has an emitter channel 1926 terminating at an emitter holder 1924, a detector channel 1927 terminating at a detector holder 1925, a strain relief 1928 and a frame hole 1929. The optical assembly 1910 fits within the resilient frame 1920. In particular, the emitter wires 1722 are disposed within the emitter channel 1926, the detector wires 1724 are disposed in the detector channel 1927, the emitter is disposed in the emitter holder 1924 and the detector 1912 and corresponding shield 1914 and light barrier 1915 are disposed in the detector holder 1925. In an embodiment, the sensor housing 1930 is a one piece silicon skin disposed over the resilient frame 1920 and the optical assembly 1910, as described with respect to FIGS. 24A-C, below. In an embodiment, the resilient frame 1920 is a polypropylene/santoprene blend. The lenses 1940 are disposed within housing apertures 1844, 1854. In an embodiment, the lenses 1940 are formed from a translucent silicone adhesive. In an alternative embodiment, the lenses 1940 are separately formed from clear silicone and glued into place with a translucent silicone adhesive.

FIGS. 21A-B, 22A-B, 23A-B further illustrate concha-clip sensor embodiments 2100, 2200, 2300 having a DB9 connector 2130 (FIGS. 21A-B), a MC8 connector 2230 (FIGS. 22A-B) or a M15 connector 2330 (FIGS. 23A-B). The sensor bodies 2110, 2220, 2330 have red and IR emitters 2112, 2212, 2312 and detectors 2114, 2214, 2314 in communication with connectors 2130, 2230, 2330 via emitter wires 2152, 2252, 2352 and detector wires 2154, 2254, 2354. Sensor ID resistors 2132, 2232, 2332 are mounted in parallel with the emitters, and can be read by a monitor generating currents below the emitter-on thresholds. Compatibility resistors 2134, 2334 can be read by other monitor types. EEPROMs 2136, 2236, 2336 programmed with various sensor information can be read by more advanced monitors. Shield wires 2156, 2256, 2356 provide conductive paths via the connectors to a common shield ground. In an embodiment, ID resistors are 12.7 KΩ, compatibility resistors are 6.81 KΩ, and EEPROMs are 1-wire, 20Kbit memories available from Maxim Integrated Products, Inc., Sunnyvale, Calif.

Figure 24A:
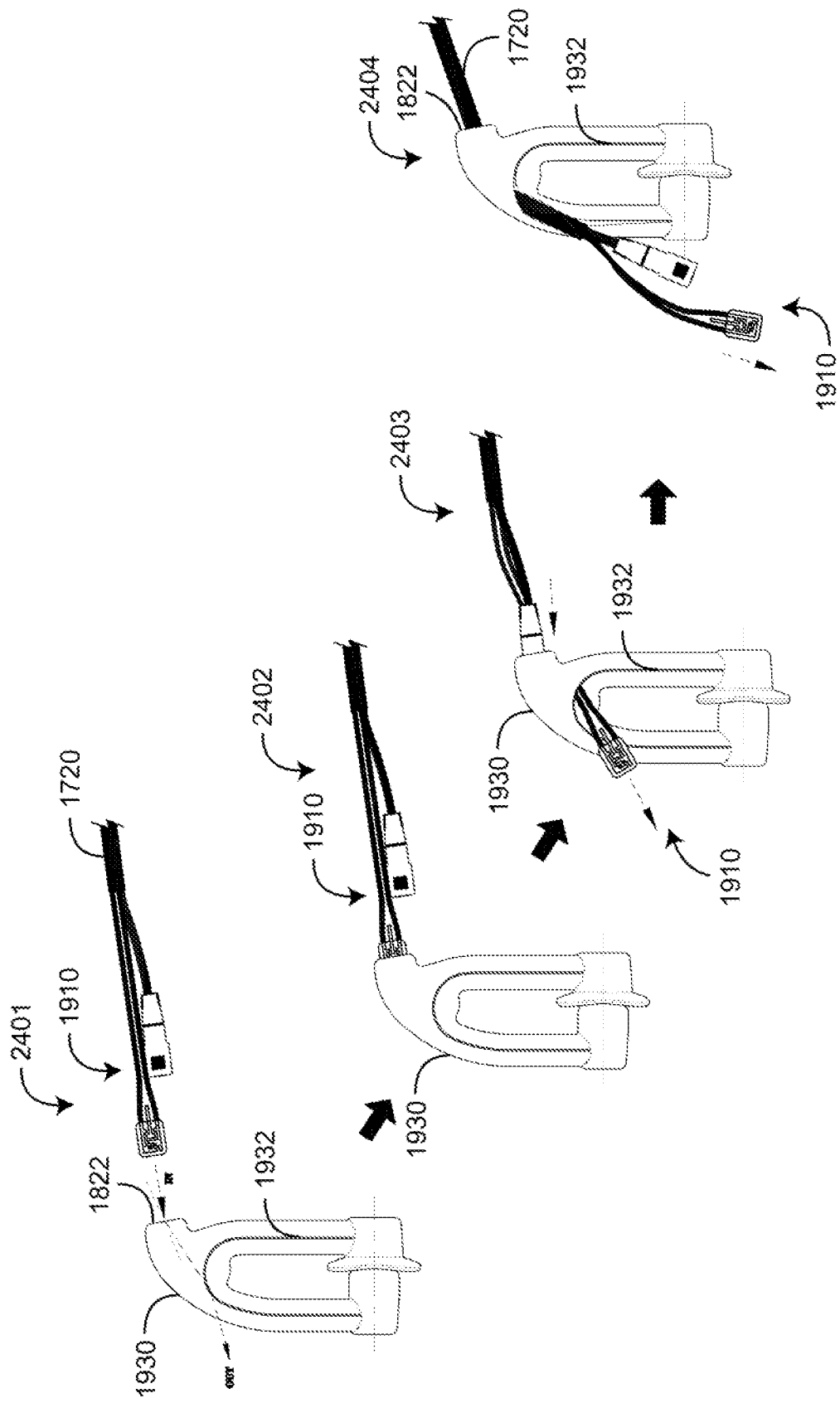
Figure 24B:
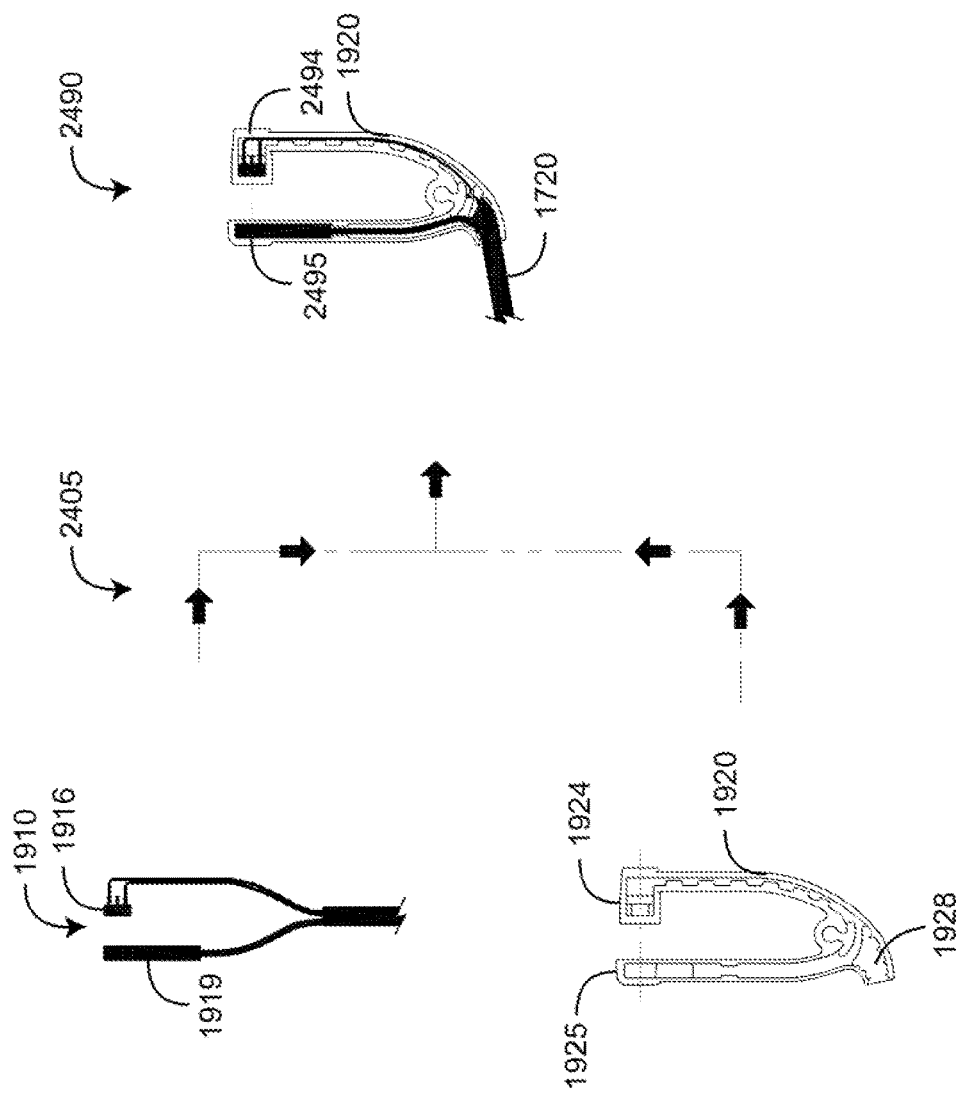
Figure 24C:
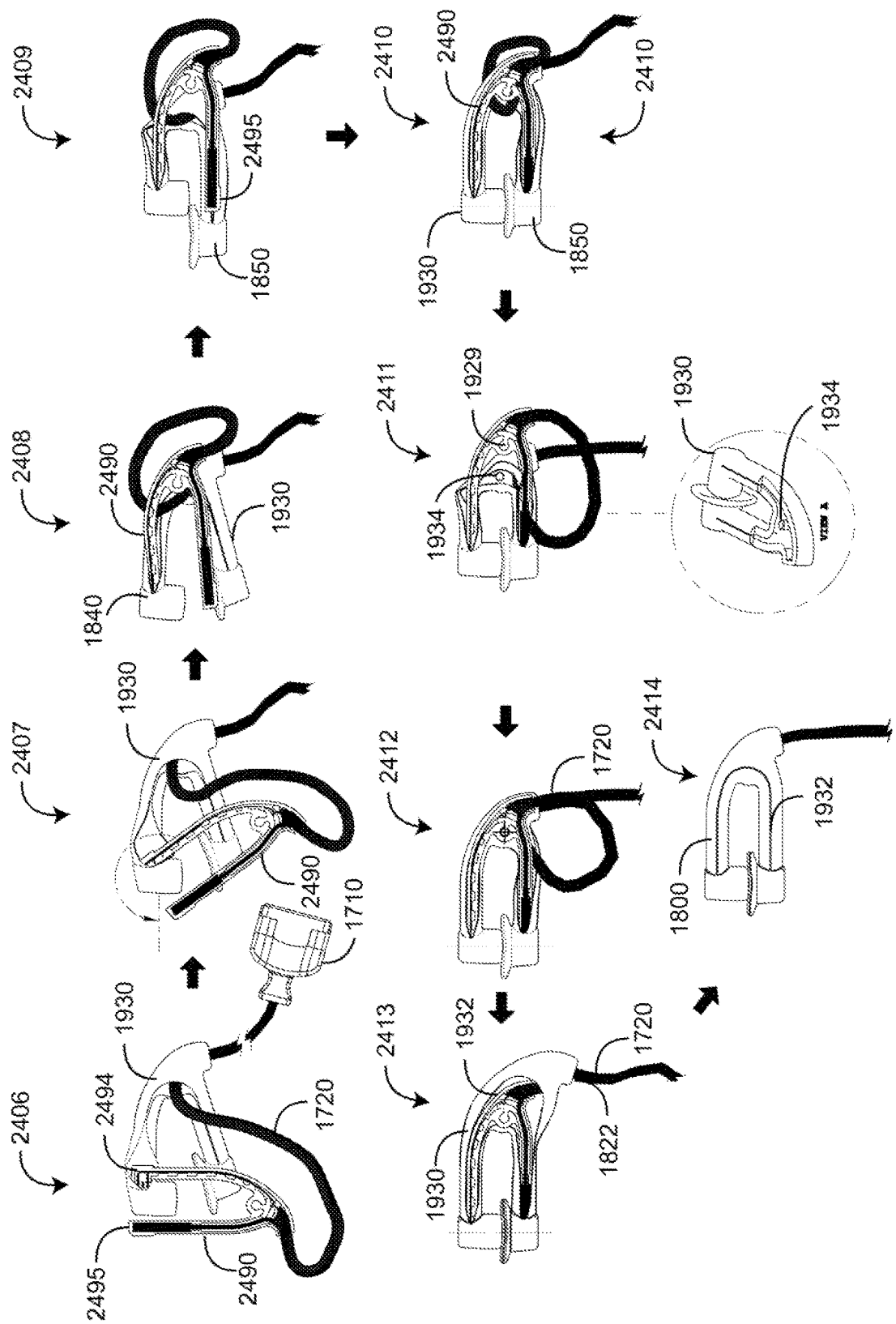
Figure 25B:
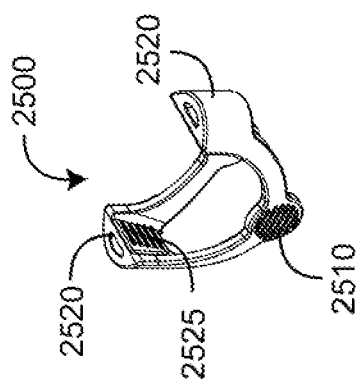
Figure 25E:
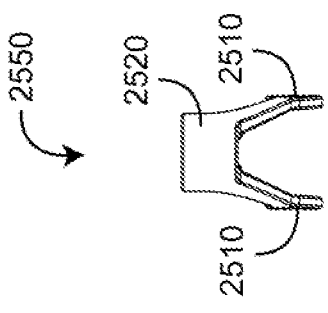
Figure 25D:
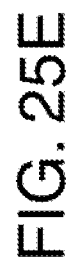
Figure 25A:
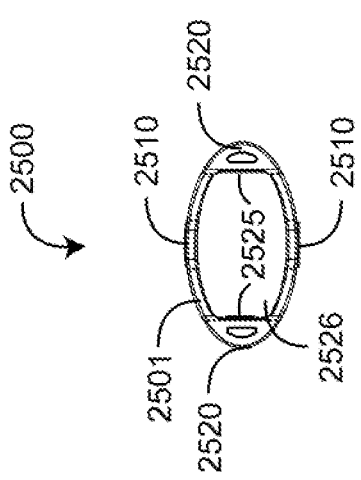
Figure 25C:
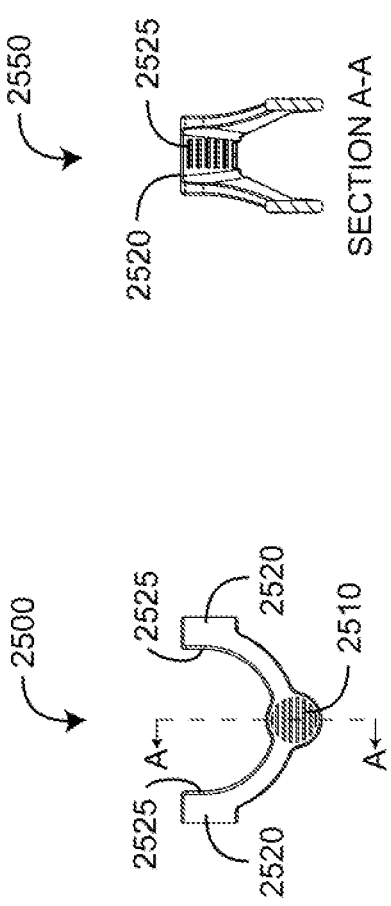
Figure 26A:
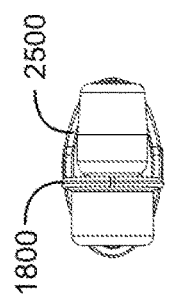
Figure 26B:
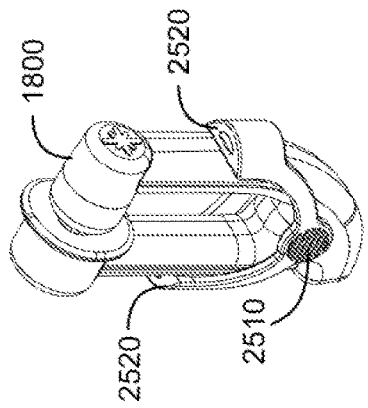
Figure 26C:
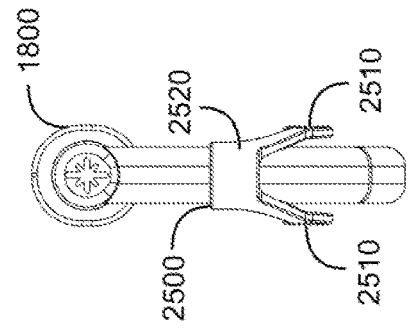
Figure 26D:
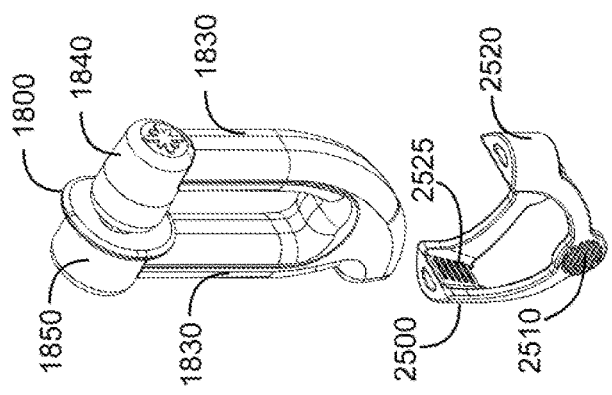
Figure 26E:
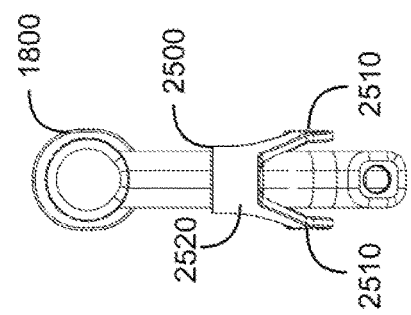
Figure 26F:
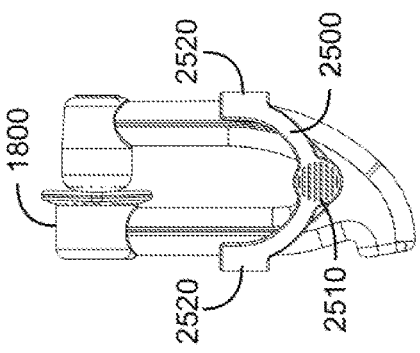

FIGS. 24A-C illustrate integration of the optical assembly 1910 disposed at the end of a sensor cable 1720, the resilient frame 1920 and the sensor housing 1930. As shown in FIG. 24A, the optical assembly 1910 is threaded into the sensor housing 1930. In particular, in a couple steps 2401-2402, the optical assembly 1910 is inserted into the sensor housing 1930 through the cable aperture 1822. In a further couple steps 2403-2404, the optical assembly 1910 and portions of the attached sensor cable 1720 are pulled through the cable aperture 1822 and out of a U-slot 1932 of the sensor housing 1930.

As shown in FIG. 24B, in a step 2405, the optical assembly 1910 is integrated with the resilient frame 1920 to form a frame assembly 2490. In particular, the detector assembly 1919 is inserted into a detector holder 1925 to form a framed detector 2495. Also, the emitter 1916 is inserted into an emitter holder 1924 to form a framed emitter 2495.

As shown in FIG. 24C, the frame assembly 2490 is integrated with the sensor housing 1930 to form the sensor body 1800. In several steps 2406-2408 the framed emitter 2494 is inserted into a pocket within the emitter housing 1840. In a couple additional steps 2409-2410, the framed detector 2495 is inserted into a pocket within the detector housing 1850. In a step 2411, a housing post 1934 is inserted into the frame hole 1929. In several additional steps 2412-2414, excess cable 1720 is removed from the sensor housing 1930 via the cable aperture 1822, and the U-slot 1932 is closed and sealed with an adhesive. The resulting sensor body 1800 is described in detail with respect to FIGS. 18A-E, above.

FIGS. 25A-E, 26A-F illustrate a force adjustment ring 2500 that slidably attaches to the sensor body 1800 so as to adjust the force of the sensor housings 1840, 1850 against concha tissue. The ring 2500 forms a generally oval opening 2526 having a pair of opposing sensor grips 2520 generally centered along a long axis of the opening 2526 and a pair of finger releases 2510 generally centered along a short axis of the opening 2526. The sensor grips 2520 have toothed faces 2525 configured to contact the sensor body legs 1830. The finger releases 2510 allow the ring to be squeezed between a finger and thumb, say, so as to compress the ring short axis, thereby lengthening the ring long axis and releasing the toothed faces 2525 from the legs 1830. In this manner, the ring 2500 can be positioned closer to or farther from the housings 1840, 1850 so as to increase or decrease the force on a concha tissue site.

FIGS. 27A-F illustrate an sensor body 2700 configured for a parallel-routed sensor cable, as compared with the sensor body 1800 (FIGS. 18A-E) configured for a perpendicular-routed sensor cable, as described above. The sensor body 2700 has a base 2710, a strain relief 2720 formed at a bottom end of the base 2710 and a pair of resilient legs 2730 extending from an opposite end of the base 2710. The strain relief 2720 has an aperture 2722 that accommodates the sensor cable 1720 (FIGS. 17A-B). An emitter housing 2740 extends from one leg 2730 and a detector housing 2750 extends from the other leg 2530. The legs 2730 accommodate cable conductors extending between a connector 1710 (FIGS. 17A-B) and an optical assembly 1910 (FIG. 19) located in the housings 2740, 2750. Each housing 2740, 2750 has an optical end having an aperture that passes light from the emitter housing 2740 to the detector housing 2750. In an embodiment, the housings 2740, 2750 fit on either side of a concha tissue site so that light is transmitted from an emitter of the optical assembly, through the concha tissue and received by a detector of the optical assembly. In an embodiment, the emitter housing 2740 fits within the ear and the detector housing outside the ear. In an embodiment, a cup 2760 extends from the optical end of the detector housing 2750. The cup 2760 has a generally circular edge and a curvature that accommodates the outside curvature of the ear. Accordingly, the cup 2760 advantageously provides a more comfortable and secure fit of the detector housing 2750 to the ear and further functions as a light shield, blocking external light sources from the detector assembly.

A sensor body 1800 (FIGS. 18A-E), 2700 (FIGS. 27A-F) is described above with respect to directly flexing resilient legs in order to space apart emitter and detector housings for placement on a concha site. In another embodiment, a pair of finger levers can extend from the legs to a position below the sensor body base opposite the resilient legs. The finger levers can be squeezed between finger and thumb so as to flex the resilient legs for concha site placement.

In a particular advantageous embodiment, a single finger lever can extend from one leg to a position below the base. This single finger lever can be squeezed using a sensor cable portion extending from the sensor body base for leverage. Such a single finger lever configuration eliminates potential discomfort from a second lever poking a patient's neck area.

An ear sensor has been disclosed in detail in connection with various embodiments. These embodiments are disclosed by way of examples only and are not to be construed as limiting the scope of the claims that follow. One of ordinary skill in art will appreciate many variations and modifications.

What is claimed is:

1. A physiological measurement device configured for placement at an ear of a user, the physiological measurement device comprising:
    a body portion;
    an extension portion connected to and extending transverse with respect to the body portion, the extension portion configured to be positioned at least partially in an ear canal of the user's ear when the physiological measurement device is in use, wherein, when the extension portion is positioned at least partially in the ear canal of the user's ear, the body portion is positioned outside of the ear canal and adjacent tissue of a concha of the user's ear; and
    at least one light emitter and at least one detector, the at least one light emitter and the at least one detector arranged in a reflective measurement configuration on the body portion of the physiological measurement device, wherein the at least one light emitter is configured to emit light towards said tissue of said concha of the user's ear when the physiological measurement device is in use, and wherein the at least one light detector is configured to output at least one signal responsive to detecting at least a portion of the emitted light after reflection from at least a portion of said tissue of said concha of the user's ear when the physiological measurement device is in use, said at least one signal indicative of at least one physiological parameter of the user.

2. The physiological measurement device of claim 1, wherein the at least one emitter comprises at least one light emitting diode (LED).

3. The physiological measurement device of claim 1, wherein the extension portion comprises an ear bud.

4. The physiological measurement device of claim 1, wherein the body portion of the physiological measurement device is larger than the extension portion.

5. The physiological measurement device of claim 1, further comprising a cable.

6. The physiological measurement device of claim 5, wherein the cable is configured to communicate said at least one signal to a monitoring device, said at least one signal usable by the monitoring device to determine said at least one physiological parameter of the user.

7. The physiological measurement device of claim 5, wherein the cable extends from the body portion.

8. The physiological measurement device of claim 1, wherein the at least one physiological parameter comprises at least one of an oxygen saturation and a pulse rate of the user.

9. The physiological measurement device of claim 1, wherein the at least one emitter and the at least one detector on the body portion are configured to be positioned outside of the ear canal and adjacent the tissue of the concha of the user's ear when an entirety of the extension portion is positioned within the user's ear canal.

10. The physiological measurement device of claim 1, wherein the extension portion does not comprise an emitter and does not comprise a detector.

11. A hearing aid comprising the physiological measurement device of claim 1.

12. A physiological measurement device configured for placement at an ear of a user, the physiological measurement device comprising:
    a body portion;
    an extension portion connected to the body portion and configured to be positioned at least partially in an ear canal of the user's ear when the physiological measurement device is in use, wherein, when the extension portion is positioned at least partially in the ear canal of the user's ear, the body portion is positioned outside of the ear canal and adjacent tissue of a concha of the user's ear; and at least one light emitter and at least one detector, wherein the body portion is configured to operably position said at least one light emitter and said at least one detector adjacent said tissue of the concha of the user's ear in a reflective measurement configuration when the extension portion is positioned at least partially in the ear canal of the user's ear, and wherein said at least one light detector is configured to output at least one signal responsive to detecting at least a portion of the emitted light after reflection from at least a portion of said tissue of said concha of the user's ear when the physiological measurement device is in use, said at least one signal indicative of at least one physiological parameter of the user.

13. The physiological measurement device of claim 12, wherein the extension portion comprises an ear bud.

14. The physiological measurement device of claim 12, wherein the body portion of the physiological measurement device is larger than the extension portion.

15. The physiological measurement device of claim 12, further comprising a cable.

16. The physiological measurement device of claim 15, wherein the cable is configured to communicate said at least one signal to a monitoring device, said at least one signal usable by the monitoring device to determine said at least one physiological parameter of the user.

17. The physiological measurement device of claim 12, wherein the at least one physiological parameter comprises at least one of an oxygen saturation and a pulse rate of the user.

18. The physiological measurement device of claim 12, wherein the body portion is configured to operably position said at least one emitter and said at least one detector outside of the ear canal and adjacent the tissue of the concha of the user's ear when an entirety of the extension portion is positioned within the user's ear canal.

19. The physiological measurement device of claim 12, wherein the extension portion does not comprise an emitter and does not comprise a detector.

20. A hearing aid comprising the physiological measurement device of claim 12.

* * * * *